US009078969B2

(12) United States Patent
Ofsthun et al.

(10) Patent No.: US 9,078,969 B2
(45) Date of Patent: Jul. 14, 2015

(54) PERITONEAL DIALYSIS SYSTEM

(75) Inventors: Norma J. Ofsthun, Lexington, MA (US); Harold F. Sandford, Groton, MA (US); Amanda K. Stennett, Waltham, MA (US); Jiunn Yeong Teo, Pleasant View, UT (US); Cheryl Ford, Ogden, UT (US); Benjamin J. Lipps, Boston, MA (US); Michael James Beiriger, Pittsburgh, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1114 days.

(21) Appl. No.: 12/873,875

(22) Filed: Sep. 1, 2010

(65) Prior Publication Data
US 2011/0060273 A1   Mar. 10, 2011

Related U.S. Application Data

(60) Provisional application No. 61/276,091, filed on Sep. 8, 2009.

(51) Int. Cl.
*B01D 63/00*  (2006.01)
*A61M 1/16*  (2006.01)
(Continued)

(52) U.S. Cl.
CPC ............... *A61M 1/1696* (2013.01); *A61M 1/28* (2013.01); *A61M 1/3482* (2014.02); *A61M 1/3486* (2014.02)

(58) Field of Classification Search
CPC ...... B01D 24/007; B01D 15/00; B01D 15/08; B01D 15/10; B01D 15/18; B01D 15/26; B01D 27/00; B01D 27/02; B01D 27/04; B01D 27/14; B01D 27/146; B01D 37/00; B01D 39/00; B01D 39/02; B01D 39/08; B01D 39/16; B01D 39/20; B01D 61/00; B01D 61/14; B01D 61/142; B01D 61/145; B01D 61/16; B01D 61/18; B01D 61/20; B01D 61/22; B01D 61/24; B01D 61/243; B01D 61/28; B01D 61/58; B01D 63/00; B01D 63/02; B01D 65/00
USPC ......... 210/641, 652, 651, 663, 669, 681, 791, 210/805, 806, 807, 195.2, 255, 257.2, 258, 210/259, 282, 316, 500.23, 500.27, 906, 210/908, 638, 634, 644, 645, 646, 321.72, 210/294, 295, 322, 323.1, 323.2, 335, 210/433.1, 500.21, 506; 604/28, 29
See application file for complete search history.

(56) References Cited

U.S. PATENT DOCUMENTS 3,825,493 A   7/1974  Brown et al.
5,350,357 A   9/1994  Kamen et al.
(Continued)

FOREIGN PATENT DOCUMENTS

WO    WO 2007/103411 A2    9/2007
WO    WO 2009/083011 A2    7/2009

OTHER PUBLICATIONS

2000, Dialysis, PDF.*
(Continued)

*Primary Examiner* — Allison Fitzsimmons
(74) *Attorney, Agent, or Firm* — Hamilton, Brook, Smith & Reynolds, P.C.

(57) ABSTRACT

A dialysate regeneration system for removing contaminants from spent dialysate according to this invention includes a dialysate circulation flow path including a pump that pumps spent dialysate through the dialysate circulation flow path, a first cartridge adapted to remove contaminants from the spent dialysate, including a first cleaning solution inlet and a first cleaning solution outlet, a second cartridge adapted to remove urea from the spent dialysate, the second cartridge including semi-permeable hollow fibers adapted for transport of urea across the walls of the semi-permeable hollow fibers and adapted to retain at least calcium, magnesium, and sodium ions in the spent dialysate, and including a second cleaning solution inlet and a second cleaning solution outlet. Ancillary to the two cartridges, the dialysate regeneration system further includes a first dialysate cleaning flow path including a pump that pumps first cleaning solution from the first cleaning solution outlet of the first cartridge through a first cleaning stage to the first cleaning solution inlet of the first cartridge, and a second dialysate cleaning flow path including a pump that pumps second cleaning solution from the second cleaning solution outlet of the second cartridge through a second cleaning stage to the second cleaning solution inlet of the second cartridge.

24 Claims, 14 Drawing Sheets

(51) Int. Cl.
*A61M 1/28* (2006.01)
*A61M 1/34* (2006.01)
*B01D 61/00* (2006.01)

(56) References Cited

U.S. PATENT DOCUMENTS

| | | | |
|---|---|---|---|
| 5,944,684 A | 8/1999 | Roberts et al. | |
| 6,254,567 B1 | 7/2001 | Treu et al. | |
| 7,867,214 B2 | 1/2011 | Childers et al. | |
| 8,777,892 B2 | 7/2014 | Sandford et al. | |
| 2002/0112609 A1* | 8/2002 | Wong | 96/131 |
| 2002/0123715 A1 | 9/2002 | Sorenson et al. | |
| 2002/0187940 A1 | 12/2002 | Masuda et al. | |
| 2003/0105424 A1* | 6/2003 | Karoor et al. | 604/29 |
| 2003/0114787 A1 | 6/2003 | Gura | |
| 2004/0019312 A1* | 1/2004 | Childers et al. | 604/4.01 |
| 2004/0182787 A1 | 9/2004 | Chevallet et al. | |
| 2005/0131332 A1* | 6/2005 | Kelly et al. | 604/4.01 |
| 2007/0060786 A1 | 3/2007 | Gura et al. | |
| 2007/0179431 A1 | 8/2007 | Roberts et al. | |
| 2007/0199898 A1* | 8/2007 | Sakai et al. | 210/647 |
| 2008/0051696 A1 | 2/2008 | Curtin et al. | |
| 2010/0314314 A1 | 12/2010 | Ding et al. | |

OTHER PUBLICATIONS

International Preliminary Report on Patentability and Written Opinion, International Application No. PCT/US2010/047548, date of mailing Mar. 22, 2012.

Office Action, U.S. Appl. No. 12/610,969, date of mailing Apr. 24, 2012.

Roberts, M., et al., "*Innovative* Peritoneal Dialysis: Flow-Thru and Dialysate Regeneration," *ASAIO Journal*, 45: 372-378 (1999).

Raja, R., et al., "Recirculation Peritoneal Dialysis with Sorbent Redy Cartridge," *Nephron*, 16: 134-142 (1976).

Gordon, A., et al., "Augmentation of Efficiency by Continuous Flow Sorbent Regeneration Peritoneal Dialysis," *Trans. Amer. Soc. Artif. Int. Organs*, 22: 599-603 (1976).

Blumenkrantz, M. J., et al., "Development of a Sorbent Peritoneal Dialysate Regeneration System—Progress Report," *Dialysis Transplantation Nephrology*, 213-219. (1978).

Blumenkrantz, M. J. et al., Applications of the Redy® Sorbent System to Hemodialysis and Peritoneal Dialysis., *Artificial Organs*: 3(3): 230-236 (1979).

Roberts, M., et al., "Regeneration of Peritoneal Dialysate (PD): A Step Towards a Continuous Wearable Artificial Kidney (CWAK)," *Journal of American Society of Nephrology*, 2(3):367 (Sep. 1991).

Notification of Transmittal of the International Search Report and the Written Opinion of the International Searching Authority for Int'l Application No. PCT/US2010/047548; Date of Mailing: Dec. 6, 2010.

Non-Final Office Action for U.S. Appl. No. 12/610,969, "Portable Peritoneal Dialysis System", dated Mar. 25, 2013, consisting of 13 pages.

Final Office Action, U.S. Appl. No. 12/610,969, mail date Sep. 12, 2012.

U.S. Non-Final Office Action dated Aug. 8, 2013 for U.S. Appl. No. 11/371,216.

O'Loughlin, J.A., et al., "In Vivo and In Vitro Degradation of Urea and Uric Acid by Encapsulated Genetically Modified Microorganisms," Tissue Engineering, 10(9/10):1446-1455 (2004).

Non-Final Office Action dated Oct. 22, 2013 for U.S. Appl. No. 12/610,969.

Notice of Allowance for U.S. Appl. No. 12/610,969, "Portable Peritoneal Dialysis System", date of mailing May 23, 2014.

International Preliminary Report on Patentability and Written Opinion, International Application No. PCT/US2009/062967 date of mailing, May 12, 2011.

* cited by examiner

PERITONEAL DIALYSIS SYSTEM

RELATED APPLICATION

This application claims the benefit of U.S. Provisional Application No. 61/276,091, filed on Sep. 8, 2009.

The entire teachings of the above application are incorporated herein by reference.

BACKGROUND OF THE INVENTION

Renal dysfunction or failure and, in particular, end-stage renal disease, causes the body to lose the ability to remove water and minerals and excrete harmful metabolites, maintain acid-base balance, and control electrolyte and mineral concentrations within physiological ranges. Toxic uremic waste metabolites including urea, creatinine, uric acid, and phosphorus accumulate in the body's tissues, which can result in a person's death if the filtration function of the kidney is not replaced.

Dialysis is commonly used to replace kidney function by removing these waste toxins and excess water. In one type of dialysis treatment-hemodialysis-toxins are filtered from a patient's blood externally in a hemodialysis machine Blood passes from the patient through a dialyzer separated by a semi-permeable membrane from an externally-supplied dialysate. Water and toxins dialyze out of the blood through the semi-permeable membrane into the dialysate, which is then discarded. Hemodialysis treatment typically lasts several hours and must be performed under medical supervision three or four times a week, requirements that significantly decrease a patient's autonomy and quality of life. Also, since hemodialysis is performed periodically instead of continuously, the patient's condition and general well-being tend to be poor both immediately before hemodialysis (when toxin levels are high) and after hemodialysis (when electrolytes are imbalanced), resulting in the patient having symptoms that range from nausea and vomiting to edema.

Peritoneal dialysis is another type of dialysis treatment used to replace kidney function in which sterile, pyrogen-free dialysis solution (dialysate) is infused into the patient's peritoneal cavity. The peritoneal membrane serves as a natural dialyzer and toxic uremic waste metabolites and various ions diffuse from the patient's bloodstream across the membrane into the dialysis solution due to their concentration gradients. At the same time, water is drawn into the peritoneal cavity by an osmotic gradient. The dialysis solution is removed, discarded and replaced with fresh dialysis solution on a semi-continuous or continuous basis. Draining, discarding and replacing the large volumes of solution needed for peritoneal dialysis is still inconvenient, unwieldy and expensive, especially for peritoneal dialysis treatment at home instead of at a treatment center.

To address this problem, devices have been designed that reconstitute used dialysate from hemodialysis and/or peritoneal dialysis solution as opposed to discarding it. The dialysate can be regenerated in a machine employing a device that eliminates urea from the solution. For example, the original REDY® (REcirculating DYalysis) Sorbent System (Blumenkrantz et al., *Artif. Organs* 3(3):230-236, 1978) consists of a sorbent cartridge having five layers through which dialysate containing uremic waste metabolites flows in order to be regenerated. The spent dialysate flows through a purification layer that removes heavy metals (e.g., copper and lead) and oxidants (e.g., chlorine and chloramine), an aluminum oxide layer containing urease bound to some of the aluminum oxide which degrades the urea in the dialysate into ammonia and carbon dioxide gas, in equilibrium with ammonium carbonate, a zirconium phosphate layer that adsorbs the ammonium ions produced from urea degradation along with other cations (e.g., sodium, potassium, magnesium and calcium), a hydrated zirconium oxide layer that binds phosphate and other anions (e.g., fluoride and sulfate) in exchange for acetate, and an activated carbon layer that adsorbs other organic compounds (e.g., creatinine and uric acid).

Typically, the ion exchange resins used in devices such as the REDY® Sorbent System adsorb not only the urea degradation products, but also essential ions such as, for example, calcium and magnesium that have diffused into the dialysate. These ions must then be rapidly replaced in the patient; however, there currently exists no easy or convenient mechanism to do so. By comparison, current sorbent-based hemodialysis machines replace these essential ions continuously using a precision pump and associated valve and control mechanisms, devices that increase the weight and complexity of a hemodialysis machine, and would present similar problems for a peritoneal dialysis system.

There is, therefore, a need for a dialysate regeneration system that is more convenient, safe and effective and that significantly improves a patient's quality of life over current devices and methods.

SUMMARY OF THE INVENTION

The present invention provides a dialysate regeneration system that can be used at home and conveniently moved from one location to another. This system can operate continuously or semi-continuously during periods of dialysis to clear uremic waste metabolites from a patient with renal dysfunction or failure, without overly depleting the patient's body of essential ions, such as, for example, calcium and magnesium.

In one embodiment, a dialysate regeneration system for removing contaminants from spent dialysate (dialysis solution) according to this invention includes a dialysate circulation flow path including a pump that pumps spent dialysate through the dialysate circulation flow path, a first cartridge adapted to remove contaminants from the spent dialysate, including a first cleaning solution inlet and a first cleaning solution outlet, a second cartridge adapted to remove urea from the spent dialysate, the second cartridge including semi-permeable hollow fibers adapted for transport of urea across the walls of the semi-permeable hollow fibers and adapted to retain at least calcium, magnesium, and sodium ions in the dialysate, and including a second cleaning solution inlet and a second cleaning solution outlet. The dialysate regeneration system further includes, in conjunction with the first cartridge, a first dialysate cleaning flow path including a pump that pumps first cleaning solution from the first cleaning solution outlet of the first cartridge through a first cleaning stage to the first cleaning solution inlet of the first cartridge, and, in conjunction with the second cartridge, a second dialysate cleaning flow path including a pump that pumps second cleaning solution from the second cleaning solution outlet of the second cartridge through a second cleaning stage to the second cleaning solution inlet of the second cartridge.

In another embodiment, a peritoneal dialysis and dialysate regeneration system according to this invention includes a dialysate circulation flow path including a first cartridge adapted to remove contaminants from spent dialysate, including a first cleaning solution outlet and a first cleaning solution inlet, a second cartridge adapted to remove urea from the spent dialysate, the second cartridge including semi-permeable hollow fibers adapted for transport of urea across the walls of the semi-permeable hollow fibers and adapted to retain at least calcium, magnesium, and sodium ions in the spent dialysate, and including a second cleaning solution outlet and a second cleaning solution inlet, and a peritoneal dialysis cycler configured to transfer a predetermined quantity of dialysate into a peritoneal cavity of a patient, direct spent dialysate from the peritoneal cavity of the patient into the first cartridge and the second cartridge, and introduce regenerated dialysate into the peritoneal cavity of the patient. The peritoneal dialysis and dialysate regeneration system further includes, in conjunction with the first cartridge, a first dialysate cleaning flow path including a pump that pumps first cleaning solution from the first cleaning solution outlet of the first cartridge through a first cleaning stage to the first cleaning solution inlet of the first cartridge, and, in conjunction with the second cartridge, a second dialysate cleaning flow path including a pump that pumps second cleaning solution from the second cleaning solution outlet of the second cartridge through a second cleaning stage to the second cleaning solution inlet of the second cartridge.

In yet another embodiment, a peritoneal dialysis system for treating a patient and removing contaminants from spent dialysate according to this invention includes a dialysate circulation flow path including a patient dialysate outlet from a peritoneal cavity of the patient, and a pump that pumps spent dialysate from the patient dialysate outlet through the dialysate circulation flow path. The peritoneal dialysis system further includes a first cartridge adapted to remove contaminants from the spent dialysate, including a first cleaning solution inlet and a first cleaning solution outlet. The peritoneal dialysis system also includes a second cartridge adapted to remove urea from the spent dialysate, the second cartridge including semi-permeable hollow fibers adapted for transport of urea across the walls of the semi-permeable hollow fibers and adapted to retain at least calcium, magnesium and sodium ions in the dialysate, and including a second cleaning solution inlet and a second cleaning solution outlet. The peritoneal dialysis system also includes a patient dialysate inlet back to the peritoneal cavity of the patient. In conjunction with the first cartridge, the peritoneal dialysis system further includes a first dialysate cleaning flow path including a pump that pumps first cleaning solution from the first cleaning solution outlet of the first cartridge through a first cleaning stage to the first cleaning solution inlet of the first cartridge. In conjunction with the second cartridge, the peritoneal dialysis system further includes a second dialysate cleaning flow path including a pump that pumps second cleaning solution from the second cleaning solution outlet of the second cartridge through a second cleaning stage to the second cleaning solution inlet of the second cartridge.

In some embodiments, the first cleaning stage can include activated carbon. In certain embodiments, the first cleaning stage can include zirconium oxide. In some embodiments, the activated carbon and zirconium oxide form a mixture. The first cartridge can be an ultrafiltration membrane cartridge. Alternatively, the first cartridge can be a microfiltration membrane cartridge. In certain embodiments, the second cleaning stage can include urease. In some embodiments, the urease can be immobilized urease. In certain embodiments, the second cleaning stage can include zirconium phosphate. In one embodiment, the urease and zirconium phosphate are integrated into at least one cartridge. In certain other embodiments, the second cleaning stage can include strong acid cation exchange resin. In some embodiments, the urease and strong acid cation exchange resin are integrated into at least one cartridge. In certain embodiments, the second cleaning stage can include an anion exchange resin. In some embodiments, the first cleaning solution can include calcium, magnesium, and sodium in concentrations about equal to or less than the calcium, magnesium and sodium concentrations in the dialysate. In certain embodiments, the second cleaning solution includes an osmotic agent. The osmotic agent can be sucrose. In some embodiments, the contaminants can include one or more of creatinine, β-2-microglobulin, and phosphate.

The invention is also directed to a method of removing contaminants from spent dialysate that includes flowing dialysate through a dialysate circulation flow path including a pump that pumps spent dialysate through the dialysate circulation flow path, a first cartridge adapted to remove contaminants from the spent dialysate, including a first cleaning solution inlet and a first cleaning solution outlet, a second cartridge adapted to remove urea from the spent dialysate, the second cartridge including semi-permeable hollow fibers adapted for transport of urea across the walls of the semi-permeable hollow fibers and adapted to retain at least calcium, magnesium, and sodium ions in the spent dialysate, and including a second cleaning solution outlet and a second cleaning solution inlet. The method further includes flowing first cleaning solution through a first dialysate cleaning flow path including a pump that pumps first cleaning solution from the first cleaning solution outlet of the first cartridge through a first cleaning stage to the first cleaning solution inlet of the first cartridge, flowing second cleaning solution through a second dialysate cleaning flow path including a pump that pumps second cleaning solution from the second cleaning solution outlet of the second cartridge through a second cleaning stage to the second cleaning solution inlet of the second cartridge.

In another embodiment, a method of peritoneal dialysis and regenerating spent dialysate includes flowing dialysate through a dialysate circulation flow path including a first cartridge adapted to remove contaminants from spent dialysate, including a first cleaning solution outlet and a first cleaning solution inlet, a second cartridge adapted to remove urea from the spent dialysate, the second cartridge including semi-permeable hollow fibers adapted for transport of urea across the walls of the semi-permeable hollow fibers and adapted to retain at least calcium, magnesium, and sodium ions in the spent dialysate, and including a second cleaning solution outlet and a second cleaning solution inlet, and a peritoneal dialysis cycler configured to transfer a predetermined quantity of dialysate into a peritoneal cavity of a patient, direct spent dialysate from the peritoneal cavity of the patient into the first cartridge and the second cartridge, and introduce regenerated dialysate into the peritoneal cavity of the patient. The method further includes flowing first cleaning solution through a first dialysate cleaning flow path including a pump that pumps first cleaning solution from the first cleaning solution outlet of the first cartridge through a first cleaning stage to the first cleaning solution inlet of the first cartridge, and flowing second cleaning solution through a second dialysate cleaning flow path including a pump that pumps second cleaning solution from the second cleaning solution outlet of the second cartridge through a second cleaning stage to the second cleaning solution inlet of the second cartridge.

In yet another embodiment, a method of treating a patient and removing contaminants from spent dialysate includes flowing dialysate through a dialysate circulation flow path including a patient dialysate outlet from a peritoneal cavity of the patient, a pump that pumps spent dialysate from the patient dialysate outlet through the dialysate circulation flow path, a first cartridge adapted to remove contaminants from the spent dialysate, including a first cleaning solution inlet and a first cleaning solution outlet, a second cartridge adapted to remove urea from the spent dialysate, the second cartridge including semi-permeable hollow fibers adapted for transport of urea across the walls of the semi-permeable hollow fibers and adapted to retain at least calcium, magnesium, and sodium ions in the dialysate, and including a second cleaning solution inlet and a second cleaning solution outlet, and a patient dialysate inlet back to the peritoneal cavity of the patient. The method further includes flowing first cleaning solution through a first dialysate cleaning flow path including a pump that pumps first cleaning solution from the first cleaning solution outlet of the first cartridge through a first cleaning stage to the first cleaning solution inlet of the first cartridge, and flowing second cleaning solution through a second dialysate cleaning flow path including a pump that pumps second cleaning solution from the second cleaning solution outlet of the second cartridge through a second cleaning stage to the second cleaning solution inlet of the second cartridge.

An advantage of this dialysate regeneration system is that it provides patients with the option of a sorbent-based peritoneal dialysis (PD) system that can be conveniently used, for example, in the patient's home. The patient can use this dialysate regeneration system with a peritoneal dialysis system at home, nocturnally if desired. Dialysate cleaning in the dialysate regeneration system enables the use of a much smaller volume of dialysate over currently available PD systems, relieving the patient from having to handle several large and heavy bags of dialysate per day. The dialysate cleaning flow paths that include separate pumps in this dialysate regeneration system enable more efficient cleaning of the dialysate as compared to prior wearable artificial kidney devices.

BRIEF DESCRIPTION OF THE DRAWINGS

The foregoing will be apparent from the following more particular description of embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

The present invention generally relates to a peritoneal dialysis system that removes uremic waste metabolites from a patient suffering from a disorder associated with the accumulation of uremic toxins (e.g., chronic kidney failure) and removes contaminants from spent dialysate. The system can be used to treat a disorder such as, for example, renal disease, including early renal disease, renal dysfunction or renal failure (e.g., end stage renal disease). As used herein, the terms "contaminants," "uremic waste metabolites," and "uremic solutes" refer to compounds, such as those containing nitrogen, produced by the body as waste products and includes compounds like urea, uric acid, creatinine, and $\beta$-2-microglobulin, and other materials. See Vanholder R. et al., *Kidney International* 63:1934-1943, (2003). Renal failure or dysfunction leads to uremic toxicity, which occurs when the levels of uremic waste metabolites in a patient are elevated compared to the levels of the toxins in individuals with normal renal function.

Figure 1:
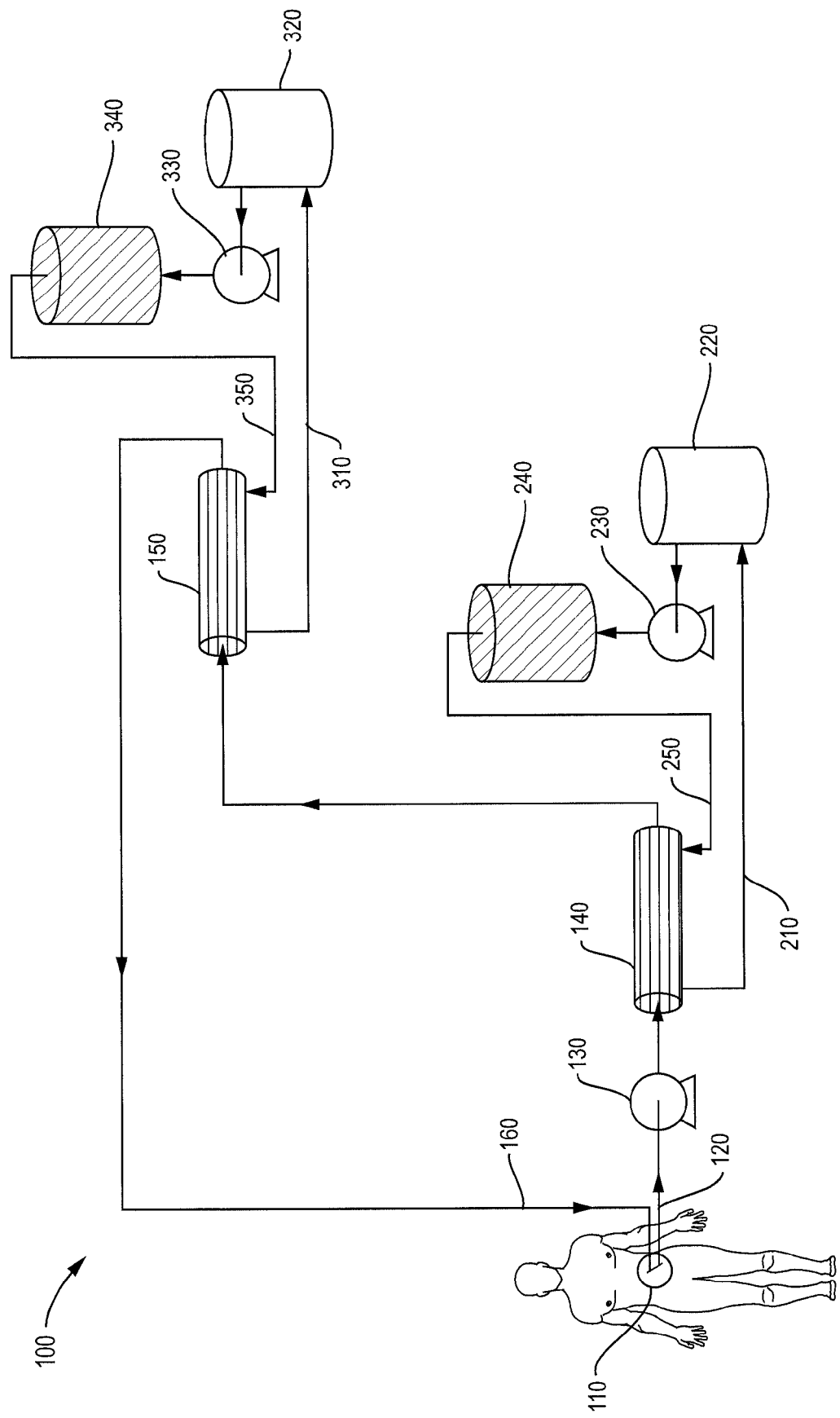
FIG. 1 is a schematic illustration of a peritoneal dialysis system according to this invention.

FIG. 1 illustrates a specific preferred embodiment of a peritoneal dialysis system according to this invention. Each of the components will be described in more detail in the description of each stage. Peritoneal dialysis system 100 for treating a patient and removing contaminants from spent dialysate comprises a dialysate circulation flow path that includes a patient dialysate outlet 120 from the peritoneal cavity 110 of the patient, and a pump 130 that pumps dialysate from the patient dialysate outlet 120 through the dialysate circulation flow path that further includes a first cartridge 140 adapted to remove contaminants from the spent dialysate, including a first cleaning solution inlet 210 and a first cleaning solution outlet 250, and a second cartridge 150 adapted to remove urea from the spent dialysate, including a second cleaning solution inlet 310 and a second cleaning solution outlet 350. Finally, the dialysate circulation flow path includes a patient dialysate inlet 160 for returning regenerated dialysate back to the peritoneal cavity 110 of the patient.

The patient dialysate outlet 120 and patient dialysate inlet 160 provide outflow from and inflow to the peritoneal cavity of the patient. These access ports can include medically appropriate plastic tubing, a double lumen catheter or two single lumen catheters. See Cruz et al., *Seminars in Dialysis*, Vol. 14, No. 5 pp. 391-394 (2001), Amerling et al., *Seminars in Dialysis*, Vol. 16, No. 4 pp. 335-340 (2003), and Amerling et al., *Seminars in Dialysis*, Vol. 14, No. 5 pp. 388-390 (2001) for examples of access ports for peritoneal dialysis. The peritoneal dialysis system also contains a volume of peritoneal dialysis solution (dialysate) that is infused into and out of the patient's peritoneal cavity 110 such that the peritoneal dialysis solution removes uremic waste metabolites that diffuse through the patient's peritoneal membrane into the peritoneal dialysis solution. A variety of peritoneal dialysis solutions can be used (e.g., Delflex®), these solutions being commercially available (e.g., Fresenius Medical Care North America, Waltham Mass.) and well-known in the art. Commercially available peritoneal dialysis solutions (e.g., Delflex®), typically contain calcium (5-7 mg/dL) and magnesium (0.6-1.8 mg/dL). A volume of about 0.5 to 3 liters of peritoneal dialysis solution can be introduced into the peritoneal cavity of the patient, and it is preferable that about 2.5 liters of the solution be infused.

The pump 130 can be a peristaltic pump or other pump where the fluid path does not contact the pump interior. Examples include, but are not limited to: Watson-Marlow 405U/L, Cole-Parmer metering peristaltic pump (HV7420040), Masterflex L/S 16, and Fresenius Medical Care M30656. The flow rate of the dialysis solution through the dialysate circulation flow path can be about 100 mL/min (milliliters per minute) to about 300 mL/min, preferably about 100 mL/min.

The first cartridge 140 is adapted to remove contaminants from the dialysate including phosphate and organic contaminants, such as, for example, creatinine and β-2-microglobulin. In a preferred embodiment, the first cartridge 140 includes semi-permeable hollow fibers. Appropriate semi-permeable hollow fiber materials include cellulose, nylon, polyvinylidene fluoride, polyvinylpyrrolidone, polysulfone, polyether sulfone, and polypropylene. A preferred embodiment includes hollow fibers with an inner diameter equal to or less than about 210 μm (micrometers), and a wall thickness equal to or less than about 40 μm, preferably made of polysulfone. The spent dialysate flows through the lumen of the hollow fibers and the contaminants in the dialysate are filtered out of the solution and are transported across the semi-permeable fiber walls. The total membrane area of the polysulfone fibers in the first cartridge 140 can be in a range of about 0.4 $m^2$ (square meters) to about 1 $m^2$, preferably about 0.5 $m^2$. The porosity of the hollow fiber walls can be defined in terms of an average pore diameter, above which a molecule will be prevented from passing through the fiber wall and will therefore be retained in the dialysate. A preferred embodiment of the first cartridge 140 can be a microfiltration membrane cartridge, with an average pore diameter for the hollow fibers in a range of about 0.05 microns to about 2.5 microns. An even more preferred embodiment of the first cartridge 140 can be an ultrafiltration membrane cartridge, with an average pore diameter for the hollow fibers in a range of about 0.003 microns to about 0.1 microns. Examples of microfiltration membrane products include GE Sepa CF PVDF MF JX, a flat sheet membrane, Koch Romicon MF 5" cartridge, a hollow fiber membrane, and Pellicon XL Durapore 0.1 micron filter module, a cassette. (GE Osmonics, Minnetonka, Minn.) (Koch Membrane Systems, Inc., Wilmington Mass.) (Millipore, Inc., Billerica Mass.). Examples of ultrafiltration membrane products include GE Sepa CF Thin Film UF JW, a flat sheet membrane, GE Sepa CF Polysulfone UF EW, a flat sheet membrane, and Amicon PM30 polyethersulfone UF disc, a flat sheet membrane.

The second cartridge 150 is adapted to remove urea from the dialysate, while retaining positive ions (cations), including, for example, calcium, magnesium, and sodium ions in the dialysate. In a preferred embodiment, the second cartridge 150 includes semi-permeable hollow fibers adapted for transport of urea across the walls (membrane) of the semi-permeable hollow fibers and adapted to retain at least calcium, magnesium, and sodium ions in the dialysate. The membrane area of the semi-permeable hollow fibers can be in a range of about 0.5 $m^2$ to about 2 $m^2$, depending on the rate of urea transport of the hollow fibers.

Figure 2:
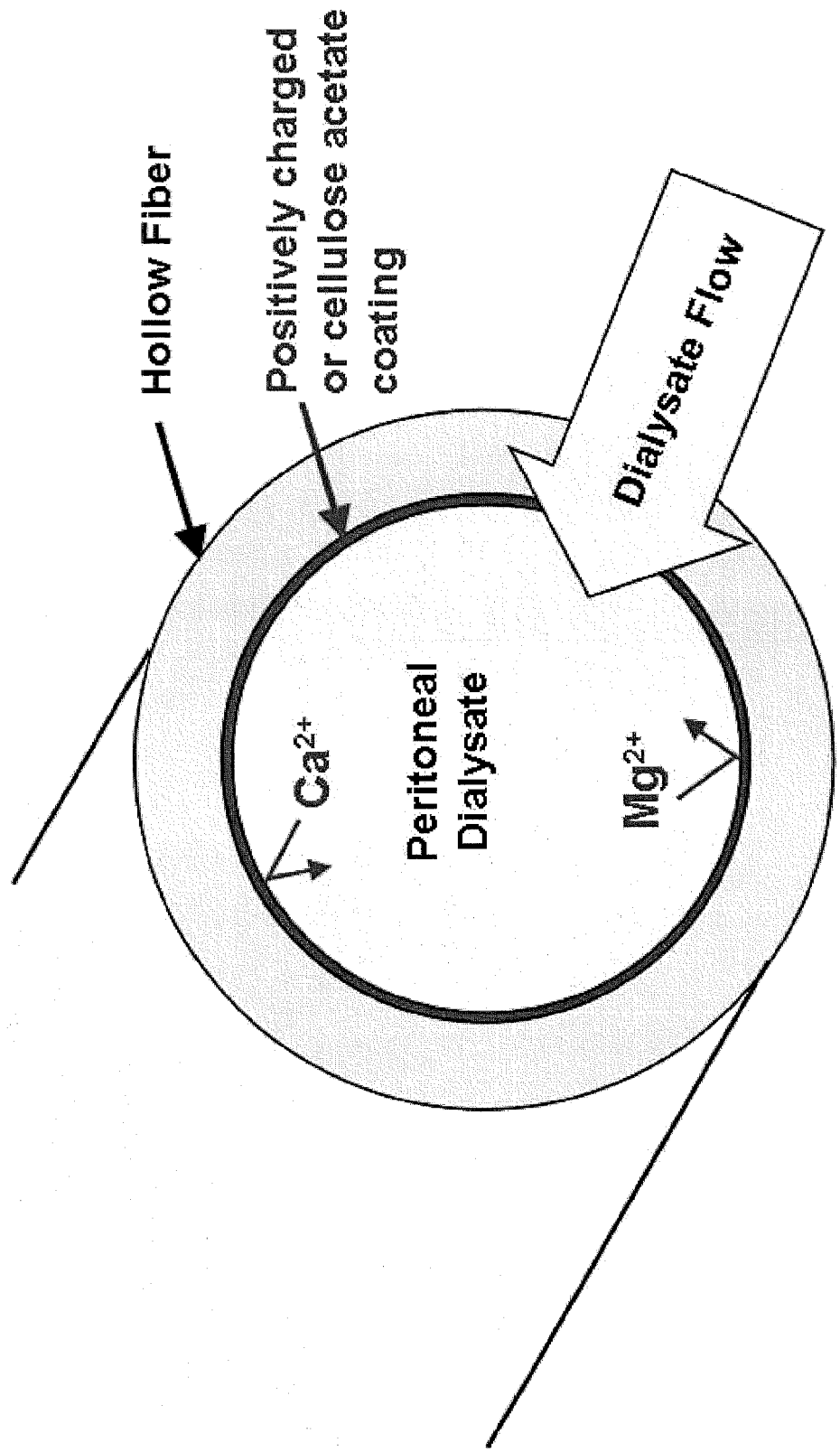
FIG. 2 is a schematic illustration of an ion rejecting hollow fiber suitable for inclusion in the peritoneal dialysis system shown in FIG. 1.

A preferred approach to cation retention in the dialysate employs hollow fibers that are fabricated from or coated with a cation-rejecting material. For example, a layer can be formed on the inside or outside of the hollow fibers by coating or co-extruding them with a cation-rejecting material. FIG. 2 illustrates a hollow fiber membrane that retains calcium and magnesium ions in the dialysate that flows through the lumen of the hollow fiber. The material forming the selective cation-rejecting layer can be, for example, esterified cellulose or acetylcellulose (cellulose acetate). In a preferred embodiment, the selective layer can be acetylcellulose, as described in German Application No. DE 10 2008 003 090.2, filed on Jan. 3, 2008, an English-language translation of which is included in U.S. Provisional Application No. 61/276,091, filed on Sep. 8, 2009, the entire contents and teachings of which are incorporated herein by reference. Briefly, a hollow fiber is produced by the phase inversion process. First, two spinning dope solutions A and B are produced. The first spinning dope solution A comprises the material for the lumen-side cation-rejecting layer of the hollow fiber membrane, and the second spinning dope solution B comprises the material for the support layer. The spinning dope solution for the support layer (the outer layer) consists of 20 wt % Udel 3500 polysulfone and 5 wt % K90 polyvinylpyrrolidone and also 1 wt % water, in solution in dimethylacetamide. The viscosity of this solution is about 11,500 mPa·s. The spinning dope for the lumen-side cation-rejecting layer consists of 30 wt % cellulose diacetate having a molecular weight of about 29 kDaltons and an acetyl content of 40%. (Sigma Aldrich, St. Louis, Mo.) It is dissolved in dimethylacetamide by stirring. The viscosity of this solution is about 15,000 mPa·s.

The two spinning dope solutions are spun in a suitable volume ratio through a composite hollow fiber die known in the art. In the hollow fiber die, the two solutions are led through mutually concentric die channels which permit the coextrusion of the inner and outer spinning dopes. The two concentric die channels surround an axial channel through which a coagulant for the two spinning dope layers is led. Water is a preferred inner coagulant. The temperature of the die pack (spin pack) is about 20° C.

After emerging from the spin pack, the hollow fiber passes through an air gap of about 250 mm before entering a water-filled coagulation bath having a temperature of about 42° C. Subsequently, the composite hollow fiber thus obtained is rinsed in a rinse bath that is temperature controlled at about 75° C. The output speed of spinning fiber is about 250 mm/s. The hollow fiber thus obtained is subsequently dried at a temperature of about 95° C. Coagulation and rinse bath volumes and spinning speed are adjusted so as to obtain a solvent-free regular hollow fiber.

The dry fiber is subsequently reeled. A bundle of the hollow fibers consists of about 2,300 fibers having a total surface area of about 0.4 $m^2$. The fiber internal diameter is about 200 μm. The fiber external diameter is about 261 μm. The thickness of the cation-rejecting layer is about 500 nm. The fibers are then moulded into a housing and potted with polyurethane to form a module ensuring independent flows along the fiber lumen and along the fiber outside surface. In a specific embodiment, the urea transport rate of cation-rejecting acetylcellulose membranes can be in a range of about 15 $g/m^2/day$ (grams per meter square per day) to about 40 $g/m^2/day$.

Alternatively, the cation-rejecting material can be a thin film composite membrane, wherein an interfacial polymerized coating is deposited on the surface of an existing membrane. An interfacial polymerized coating can be deposited by flowing an aqueous solution of a compound containing more than one amine group, such as, for example, p-phenylenediamine, through the inside of a hollow fiber, followed by flowing a non-aqueous solution of an acid chloride containing two or more carbonyl groups and capable of forming a covalent bond with amine, such as, for example, trimesoyl chloride, through the inside of the hollow fiber. In a preferred embodiment, about 0.2-2.0%, more preferably about 2.0% by weight of p-phenylenediamine dissolved in water, followed by about 0.5-2.0%, more preferably about 2.0% by weight of trimesoyl chloride dissolved in hexane, can be used to make a thin film composite membrane on the lumen side of a polysulfone hollow fiber with an ultrafiltration molecular weight cutoff equal to or less than about 50 kDa ($10^3$ Daltons), an internal diameter equal to or less than about 210 µm, and a wall thickness equal to or less than about 40 µm. In a specific embodiment, the urea transport rate of cation rejecting membranes with an interfacial polymerized coating can be in a range of about 20 g/m$^2$/day (grams per meter square per day) to about 60 g/m$^2$/day.

Turning back to FIG. 1, in conjunction with the first cartridge 140, the peritoneal dialysis system further includes a first dialysate cleaning flow path including a pump 230 that pumps first cleaning solution from the first cleaning solution inlet 210 of the first cartridge 140 through a first cleaning stage 240 to the first cleaning solution outlet 250 of the first cartridge 140. The first dialysate cleaning flow path can also include an optional first cleaning solution reservoir 220. In one embodiment, the total volume of the first cleaning solution is about 1 Liter. The first cleaning solution can be an aqueous solution that can include calcium, magnesium, and sodium in concentrations about equal to the calcium, magnesium and sodium concentrations in the dialysate, in order to maintain an equilibrium in the concentrations of these cations across the membrane walls of first cartridge 140, and therefore prevent removal of these cations from the dialysate. Alternatively, the first cleaning solution can include calcium, magnesium, and sodium in lower concentrations than the calcium, magnesium and sodium concentrations in the dialysate, if some removal of these cations from the dialysate is desired.

The pump 230 that pumps the first cleaning solution can be a gear pump, a diaphragm pump, a roller pump, or any other suitable pump. Examples of gear pumps include, but are not limited to: Cole-Parmer miniature gear pump EW0701220, Haight 6US Stainless Steel gear pump, Tuthill D series gear pump, and Fresenius Medical Care 565342. (Cole-Parmer, Vernon Hills, Ill.) (Haight Pumps, Evansville Wis.) (Tuthill, Alsip Ill.). In a preferred embodiment, the pump 230 pumps the first cleaning solution through the first dialysate cleaning flow path through the shell side (outside of the hollow fibers) of cartridge 140 in a direction that is countercurrent to the flow of dialysate through the lumen of the hollow fibers, at a flow rate that is typically at least equal to the dialysate flow rate, and preferably greater than the dialysate flow rate, up to about 800 mL/min.

During operation of the peritoneal dialysis system 100, the first cleaning solution accumulates contaminants such as, for example, creatinine, β-2-microblobulin, and phosphate from the dialysate. The first cleaning stage 240 is adapted to remove these contaminants from the first cleaning solution, to maintain a concentration gradient between the dialysate and the first cleaning solution, and therefore continue cleaning the dialysate.

To remove organic contaminants, the first cleaning stage 240 includes activated carbon, typically charcoal. Preferably, the activated carbon has a large surface area per unit volume, a wide range of pore sizes for adsorbing various size uremic toxins, and a high purity and/or USP grade. High purity of the carbon can be achieved through multiple acid and/or water washes to remove any water soluble impurities. It is also advantageous for the carbon to be in the form of small granules or a coarse powder in order to have less flow restriction (pressure drop) and optimal solute transport. Examples of appropriate activated carbon include: Nuchar® Aquaguard 40 (MeadWestvaco, Glen Allen, Va.), Norit® ROX, and Norit® E Supra (Norit Americas, Marshall, Tex.). A preferred activated carbon is acid-washed pyrolyzed coal-derived activated carbon, such as that marketed by Calgon Carbon Corporation, Pittsburgh, Pa.

Phosphorus, as phosphate ($PO_4^{3-}$, $HPO_4^{2-}$, and $H_2PO_4^-$), and sulfate ($SO_4^{2-}$) can be removed by binding to anion exchange resins, or to hydrous zirconium oxide (ZrO). Appropriate anion exchange resins include DOWEX™ 1 (hydroxide form), M-43, 21K XLT, Marathon™ MSA, and M4195 (copper form) (Dow Chemical, Midland, Mich.), and Amberlite™ 96 (Rohm and Haas, Philadelphia, Pa.). In a preferred embodiment, hydrous zirconium oxide (e.g., zirconium oxide in the acetate or carbonate counter ion form) can be used to bind phosphate and sulfate. Current data suggests that zirconium oxide does not substantially adsorb calcium and magnesium. In one embodiment, the activated carbon powder and hydrous zirconium oxide powder can be in separate compartments in the first cleaning stage 240, or the activated carbon powder and hydrous zirconium oxide powder can be layered. In a preferred embodiment, the activated carbon powder can be mixed with the hydrous zirconium oxide powder prior to loading the mixture into the first cleaning stage 240.

In conjunction with the second cartridge 150, the peritoneal dialysis system further includes a second dialysate cleaning flow path including a pump 330 that pumps second cleaning solution from the second cleaning solution inlet 310 of the second cartridge 150 through a second cleaning stage 340 to the second cleaning solution outlet 350 of the second cartridge 150. The second dialysate cleaning flow path can also include an optional second cleaning solution reservoir 320. The second cleaning solution is typically an aqueous solution. In one embodiment, the total volume of the second cleaning solution is in a range of about 1.5 Liters to about 2 Liters. The pump 330 that pumps second cleaning solution can be of the same type as described above for pump 230. In a preferred embodiment, the pump 330 pumps the second cleaning solution through the second dialysate cleaning flow path through the shell side (outside of the semi-permeable hollow fibers) of cartridge 150 in a direction that is countercurrent to the flow of dialysate through the lumen of the hollow fibers, at a flow rate that is typically at least equal to the dialysate flow rate, and preferably greater than the dialysate flow rate, up to about 800 mL/min.

During operation of the peritoneal dialysis system 100, the second cleaning solution accumulates urea from the dialysate. The second cleaning stage 340 is adapted to remove urea from the second cleaning solution, to maintain a concentration gradient between the dialysate and the second cleaning solution, and therefore continue cleaning the dialysate.

Urea can be removed by adsorption onto a strong acid cation exchange resin or onto an ion exchange sorbent, or by initially breaking down the urea into ammonia and carbon dioxide gas with a urea-degrading enzyme followed by removal of the ammonia byproduct by adsorption onto the strong acid cation exchange resin or the ion exchange sorbent, and venting of the carbon dioxide to the atmosphere. The urea-degrading enzyme can be naturally occurring (e.g., urease from jack beans, other seeds or bacteria), or produced by recombinant technology (e.g., in bacterial, fungal, insect, or mammalian cells that express and/or secrete urea-degrading enzymes), or produced synthetically (e,g., synthesized).

In one embodiment, the urea-degrading enzyme can be urease. Immobilizing the urease is generally preferred, because immobilization stabilizes the urease while retaining its enzymatic activity, and reduces the likelihood of the urease becoming entrained in the stream of second cleaning solution and producing ammonia downstream of the second cleaning stage, away from the ammonia sorbent. Urease can be immobilized by binding it to aluminum oxide, (e.g., SORB, HISORB, SORB Technology, Inc., Oklahoma City Okla.), or to a resin, such as, for example, Amberzyme™ (Rohm and Haas, Philadelphia Pa.). The enzyme (e.g., urease) can also be chemically attached to the membrane or, alternatively, to porous beads or a resin. This attachment both stabilizes the enzyme for extended use and, in the case of attachment to porous beads or resin, allows the urease to be filled and/or replaced in the device. In particular, urease can be chemically attached to the exterior of the polysulfone hollow fiber membrane or to separate fibers or resins. Attachment can be through reactive pendant groups of amino acid portions of the enzyme such as thiol groups, amino groups, or carboxylic acid groups that will not significantly affect the catalytic site. Chemistries that can be used to immobilize enzymes or cross-linked enzyme crystals (CLECs) are well-known in the art (see e.g., J. Jegan Roy and T. Emilia Abraham, *Strategies in Making Cross-Linked Enzyme Crystals*, Chemical Reviews, 104(9):3705-3721 (2004)). In addition, urease can be used in its crystallized form and be mixed with the ion exchange resin or sorbent, for example, for degradation of the urea. In a preferred embodiment, urease enzyme derived from jack bean meal can be immobilized by cross-linking with polyethylenimine, as described in U.S. application Ser. No. 12/552,332, filed on Sep. 2, 2009.

The ammonia produced in the enzymatic breakdown of urea can be toxic in concentrations above about 2000 μg/dL (micrograms/deciliter), and also alters the pH away from the physiological pH, inhibiting the enzymatic activity of urease. Therefore, ammonia needs to be removed, and can be removed either by adsorption onto polymeric strong acid cation exchange resins, such as, for example, sulfonic acid substituted polystyrene cross-linked with divinyl benzene, or onto an ion exchange sorbent, such as, for example, zirconium phosphate. Any strong acid cation exchange resin with sufficient ammonia (ammonium ion) binding capacity and purity is suitable. Specific examples of strong acid cation exchange resin include Amberlite™ IRN 77, IRN 97, IRN 99, IR 120, UP 252, CG 15, CG 120, IRC 50, IR 200, and IRA 900 (Rohm and Haas, Philadelphia, Pa.), or comparable resins manufactured by Dow Chemical, Mitsubishi, Purolite, Sybron, and Lanxess.

In a preferred embodiment, the ammonia can be removed by adsorption onto zirconium phosphate. In a more preferred embodiment, zirconium phosphate with improved ammonia binding capacity is prepared as described in U.S. application Ser. No. 12/569,485, filed on Sep. 29, 2009. An advantageous property of zirconium phosphate is that it helps control the pH in the vicinity of the urease, maintaining it at or near physiological pH, and therefore maintaining the enzymatic activity of the urease. In a preferred embodiment, the urease and zirconium phosphate are integrated into at least one cartridge.

In another embodiment, ammonia can be removed by adsorption onto polymeric strong acid cation exchange resins. In a preferred embodiment, the urease and strong acid cation exchange resin are integrated into at least one cartridge. In this specific embodiment, the second cleaning stage includes an anion exchange resin, to control the pH in the vicinity of the urease, maintaining it at or near physiological pH, and therefore maintaining the enzymatic activity of the urease. Appropriate anion exchange resins include DOWEX™ 1 (hydroxide form), M-43, 21 K XLT, Marathon™ MSA, and M4195 (copper form) (Dow Chemical, Midland, Mich.), and Amberlite™ 96 (Rohm and Haas, Philadelphia, Pa.).

Polymeric strong acid cation exchange resins or ion exchange sorbents bind ammonia in the form of ammonium ion ($NH_4^+$), and the ability of the resin or sorbent to bind ammonium ion is reduced by competition for binding sites from other positively charged ions (cations), thus requiring larger amounts of ammonia-removing resins or sorbents, and increasing the weight of the cartridge. Therefore, it is preferable to exclude cations from the portion of the cartridge that contains the urease and cation exchange resin or zirconium phosphate sorbent. Cation retention in the dialysate has the additional benefit that the patient's system is not overly depleted of essential ions, such as, for example, calcium ($Ca^{+2}$) and magnesium ($Mg^{+2}$). Therefore, in a preferred embodiment, as described above, the second cartridge 150 includes semi-permeable hollow fibers that are fabricated from or coated with a cation-rejecting material that inhibits the transport of cations in either direction across the semi-permeable hollow fibers.

Retaining cations in the dialysate, while having the advantages discussed above, can also generate an osmotic pressure across the hollow fiber wall, due to the concentration of dissolved solutes in the dialysate, that needs to be balanced on the shell side. Otherwise, liquid will be driven to flow into the lumen side of the hollow fibers, thereby increasing the volume of dialysate, which is undesirable for several reasons, such as the limited capacity of the patient's peritoneal cavity. Osmotic pressure can be balanced with a substance that is non-toxic, does not react with the urease or ammonia sorbent, and, most importantly, has a high enough molecular weight that it does not cross membrane wall into the lumen side of the hollow fiber. Appropriate osmotic agents include sucrose and other polysaccharides, such as, for example, polydextrin and icodextrin, and raffinose. A preferred osmotic agent is sucrose, because it is not substantially transported across the cation-rejecting hollow fiber walls. In a preferred embodiment, the osmotic agent can be mixed in with the strong acid cation exchange resins or ion exchange sorbents.

The peritoneal dialysis system described herein can be small enough to be portable. Each cleaning stage can have a volume in a range of about 250 mL to about 750 mL, and a weight in a range of about 200 g to about 900 g. In an alternative embodiment, the peritoneal dialysis system can be used as a dialysate regeneration system for removing contaminants from spent dialysate stored in a tank, that is, while the system is not connected to a patient.

Figure 11:
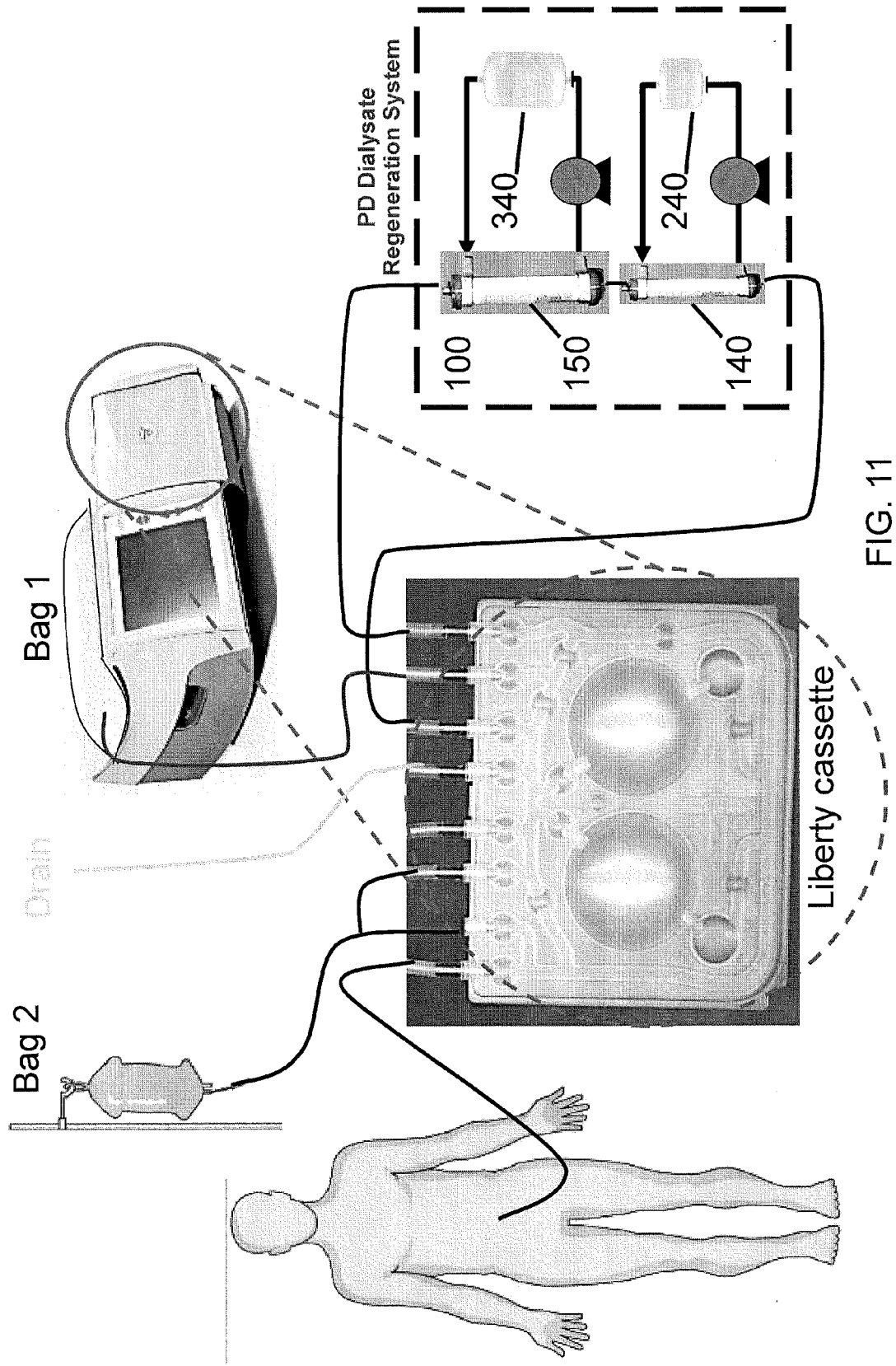
FIG. 11 is a schematic diagram of a peritoneal dialysis system including a cycler and a dialysate regeneration system.

In yet another embodiment, a peritoneal dialysis and dialysate regeneration system according to this invention includes a dialysate circulation flow path including a first cartridge adapted to remove contaminants from spent dialysate, the first cartridge including a first cleaning solution outlet and a first cleaning solution inlet, a second cartridge adapted to remove urea from the spent dialysate, the second cartridge including semi-permeable hollow fibers adapted for transport of urea across the walls of the semi-permeable hollow fibers and adapted to retain at least calcium, magnesium, and sodium ions in the spent dialysate, and including a second cleaning solution outlet and a second cleaning solution inlet, and a peritoneal dialysis cycler configured to transfer a predetermined quantity of dialysate into a peritoneal cavity of a patient, direct spent dialysate from the peritoneal cavity of the patient into the first cartridge and the second cartridge, and introduce regenerated dialysate into the peritoneal cavity of the patient. A schematic of the peritoneal dialysis system including a cycler is shown in FIG. 11. A suitable cycler is described in U.S. application Ser. Nos. 11/513,618 and 11/515,359, both filed Aug. 31, 2006, and available as the Liberty® cycler from Fresenius Medical Care North America. Briefly, the cycler transfers predetermined amounts of peritoneal dialysis solution in and out of the patient's peritoneal cavity, and in and out of several bags attached to the cycler, by means of a cassette, shown in FIG. 11, which controls the flow paths for the respective transfers of dialysis solution. Bag 1 is located on top of the cycler. The top of the cycler also includes a scale, which enables the delivery of predetermined weights (and hence volumes) of dialysis solution. The scale also includes a heater, which enables the delivery of warm dialysis solution into the patient's peritoneal cavity.

Figure 12:
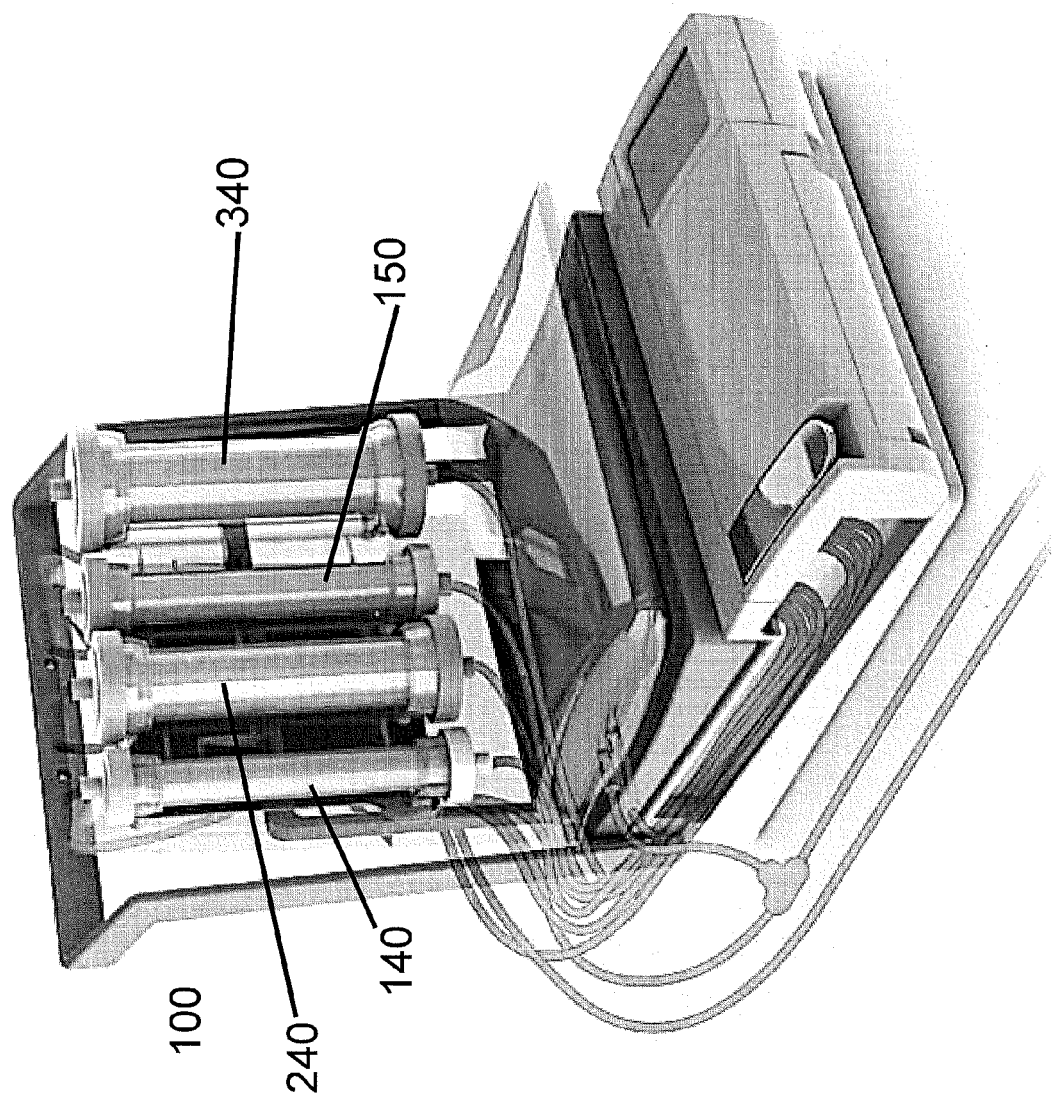
FIG. 12 is an illustration of a peritoneal dialysis dialysate regeneration system.
Figure 13A:
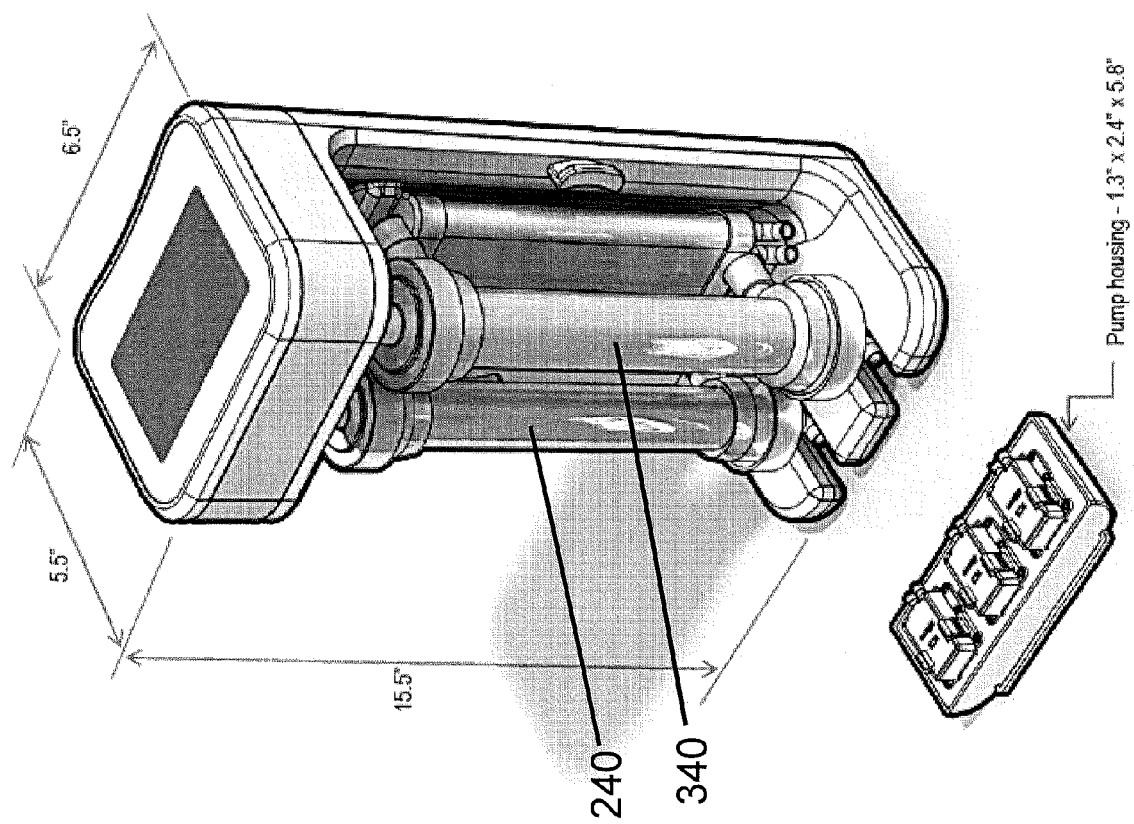
FIG. 13A is an illustration of a compact peritoneal dialysis dialysate regeneration system.
Figure 13B:
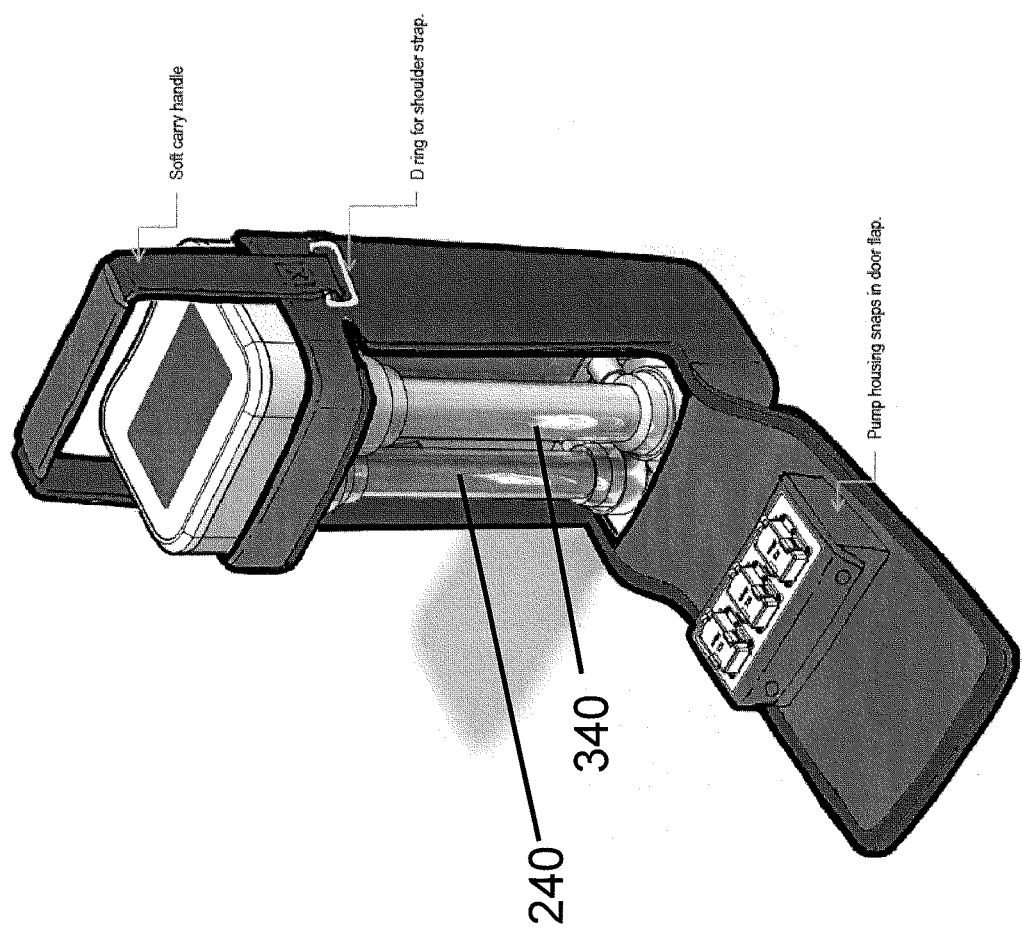
FIG. 13B is an illustration of the compact dialysate regeneration system shown in FIG. 13A fitted into a carrying case.

An embodiment of a compact peritoneal dialysis dialysate regeneration system 100 is shown in FIG. 12. FIGS. 13A-B show the embodiment shown in FIG. 1 configured in a carrying case.

Turning back to FIG. 11, a preferred method of use of the portable peritoneal dialysis system including a cycler and peritoneal dialysis dialysate regeneration system 100 can include pumping about 2.5 L of dialysate from bag 2 into bag 1 on heater, then pumping about 2.5 L of dialysate from bag 1 on heater to the peritoneal cavity of the patient for a 2 hour dwell time. The method also includes pumping about 2.5 L of dialysate from bag 2 into bag 1 on heater, shortly before it is needed. After the 2 hour dwell time, the method includes pumping spent dialysate from the patient into bag 2, and filling the patient's peritoneal cavity again with dialysate from bag 1 for a second dialysis cycle. Then, the spent dialysate from bag 2 is regenerated by passing through dialysate regeneration system 100, and delivered into bag 1 at about 100 mL/min. The volume delivered into bag 1 after the first regeneration cycle is recorded, and any ultrafiltrate (excess fluid) is drained. The method then includes pumping the remaining spent dialysate into bag 2. The regeneration cycle is then repeated, for a total of 3 passes of the spent dialysate through regeneration system 100, with regenerated dialysate finishing up in bag 1. Then the method includes pumping spent dialysate from the patient into bag 2, and filling the patient from heated bag 1 containing the regenerated dialysate, twice, for a total of 4 peritoneal dialysis treatments of the patient over an 8 hour period, nocturnally if desired.

An alternative method of use of the portable peritoneal dialysis dialysate regeneration system during one dialysis cycle can include infusing a volume of dialysate into the patient's peritoneal cavity, waiting for a dwell time of about 2 hours, draining a volume of dialysate approximately equal to the volume of fluid (ultrafiltrate) accumulated in the patient's peritoneal cavity during the dwell time, typically about 0.8 liters, circulating the dialysate through the portable peritoneal dialysis dialysate regeneration system continuously for about 8 hours, draining the entire volume of dialysate, infusing another volume of dialysate into the patient's peritoneal cavity, waiting for a dwell time of about 2 hours, and then draining the dialysate out of the patient's peritoneal cavity, leaving the cavity relatively dry for about 12 hours before beginning another peritoneal dialysis cycle. It will be noted that the peritoneal dialysis system circulates dialysate for a portion of the peritoneal dialysis cycle, but the cycle can also include periods when the dialysate is not being circulated. This type of cycle is referred to herein as semi-continuous operation of the portable peritoneal dialysis system.

Although not shown in FIG. 1, in an alternative embodiment, the system can include a bypass flow path, bypassing the patient while cleaning the dialysate. In another embodiment, also not shown in FIG. 1, the system can include bypass flow paths around the first and second cartridges, to clean the dialysate using only one of the first or second cartridge.

EXEMPLIFICATION

Phosphate and Creatinine Removal

Figure 3:
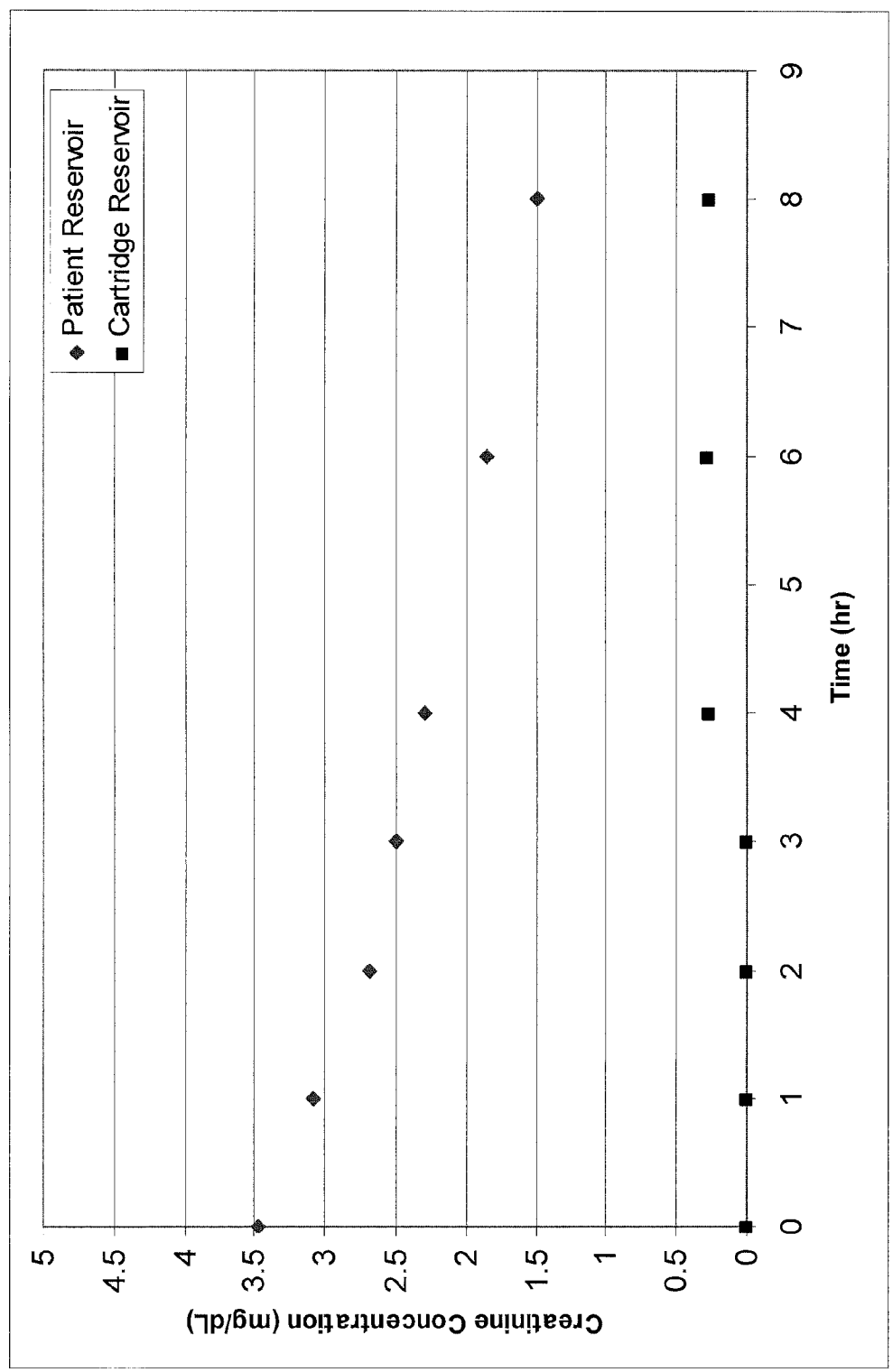
FIG. 3 is a graph of creatinine concentration as a function of time in an experimental system.

A simulated contaminated dialysate was prepared by adding 1.27 g creatinine and 5.50 g phosphoric acid to 32 L of RO water and mixing. The first cleaning stage contained 63 g of zirconium oxide and 50 g activated carbon, mixed together. The first cleaning solution reservoir contained 2 L of RO water and the first cartridge was a dialyzer, Fresenius Hemoflow F40S, with a membrane area of 0.7 $m^2$. The dialysate was pumped with a peristaltic pump at a flow rate of 94 mL/min. The first cleaning solution liquid was pumped with a gear pump at a flow rate of 189 mL/min. Both flow rates were measured via timed collection. An adjustable clamp was placed at the dialyzer lumen exit port to maintain equal hydrostatic pressure and prevent ultrafiltration. Samples were collected from each reservoir at various times and analyzed for phosphorus and creatinine concentration using an automated blood chemistry analyzer (Hitachi 911). The graph of creatinine concentration as a function of time in the dialysate (patient reservoir) and in the first cleaning solution (cartridge reservoir) is shown in FIG. 3. The creatinine concentration in the dialysate steadily decreased over 8 hours, while the creatinine concentration in the first cleaning solution remained low up to about 4 hours, because the creatinine was continually removed by the activated carbon, and then increased slightly as the activated carbon became increasingly saturated.

Figure 4:
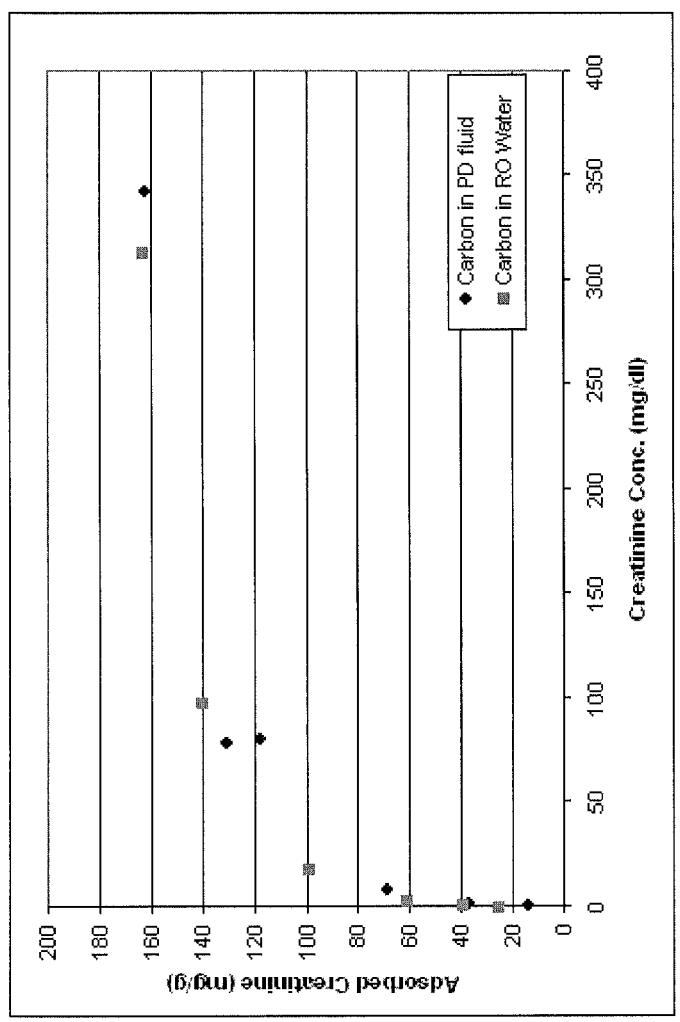
FIG. 4 is a graph of creatinine adsorbed on activated carbon as a function of creatinine concentration dissolved in dialysate and dissolved in deionized water.

FIG. 4 is a graph of creatinine adsorbed on activated carbon as a function of creatinine concentration dissolved in dialysate (PD fluid) and dissolved in deionized water (RO water), showing that the ionic concentration in peritoneal dialysis fluid does not affect the ability of activated carbon to adsorb creatinine.

Figure 5:
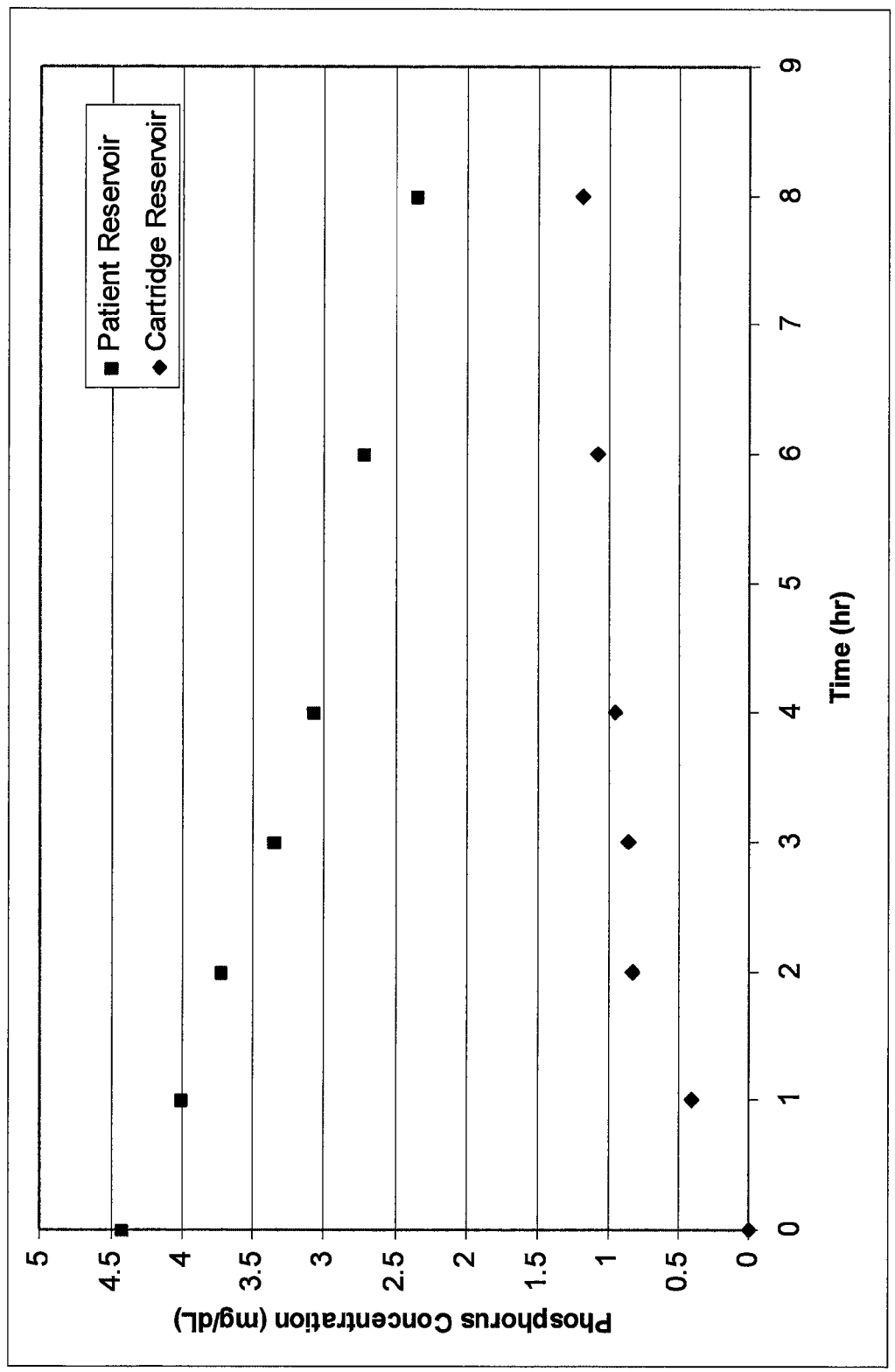
FIG. 5 is a graph of phosphorus concentration as a function of time in an experimental system.

A graph of phosphorus concentration as a function of time in the dialysate (patient reservoir) and in the first cleaning solution (cartridge reservoir) is shown in FIG. 5. The phosphorus concentration in the dialysate steadily decreased over 8 hours, while the phosphorus concentration in the first cleaning solution increased slightly as the zirconium oxide became increasingly saturated.

β-2-Microglobulin Removal

Figure 6:
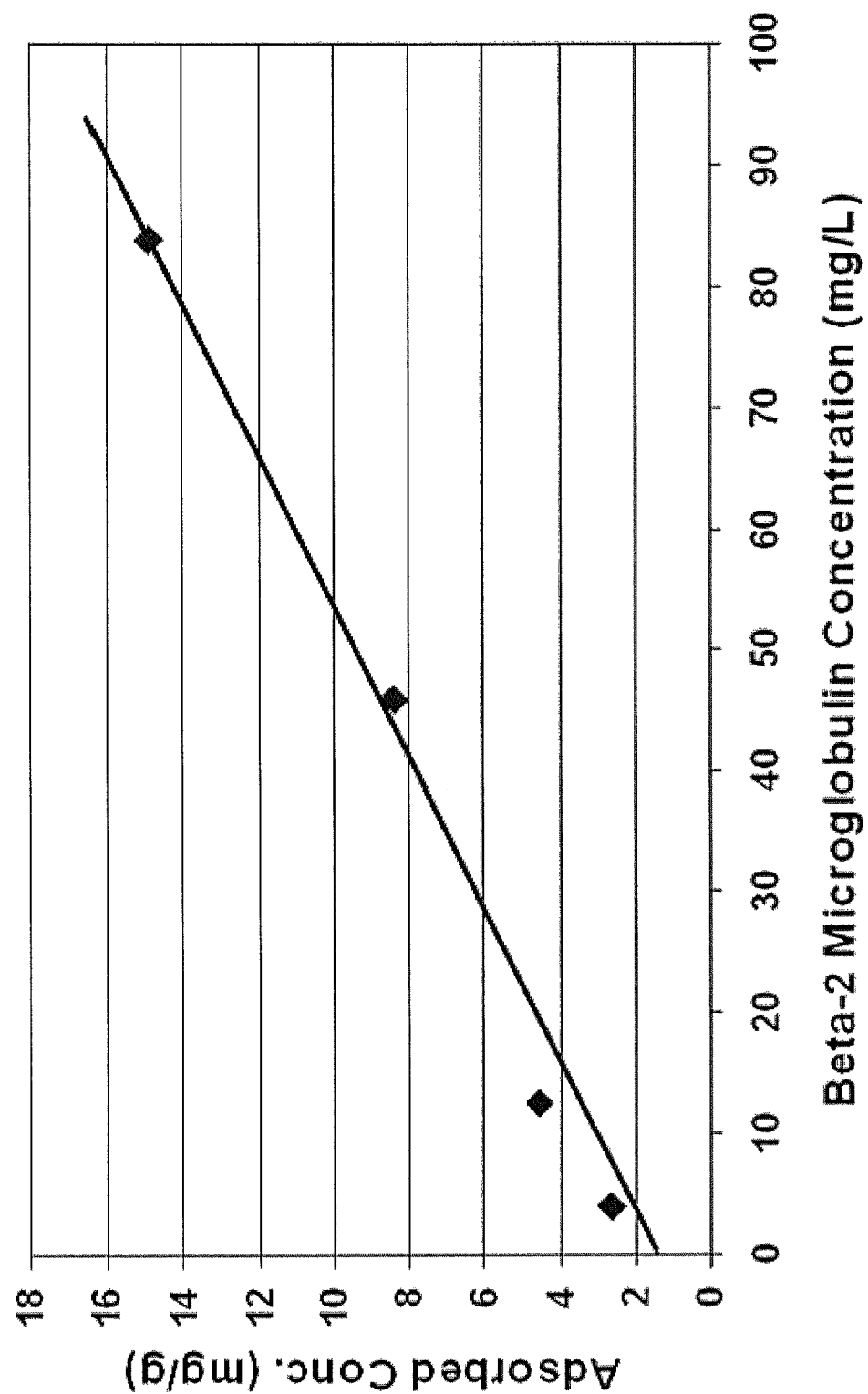
FIG. 6 is a graph of $\beta$-2-microglobulin adsorbed on activated carbon as a function of $\beta$-2-microglobulin concentration in an experimental system.

Purified β-2-microglobulin (β2M) was combined with PD fluid (Delflex 1.5% dextrose low (0.6 mg/dL) Mg, low (5 mg/dL) Ca) to get a solution of 1 mg/mL β2M. Seven test tubes were prepared by adding between 0 and 0.8 mL of β2M solution, filling to 1.5 mL with PD fluid, and mixing. To each tube, approximately 17 mg of activated carbon was added and mixed overnight. β2M solution concentrations in each tube was later measured using a standard Coomassie dye with albumin as a calibrator (Pierce Biotechnology Catalog No. 23238). The amount of β2M bound (adsorbed) was calculated from the difference between initial and final β2M concentrations. FIG. 6 shows a graph of β-2-microglobulin adsorbed on activated carbon as a function of initial β-2-microglobulin concentration.

Sodium Effect on Ammonia Binding by Zirconium Phosphate

Figure 7:
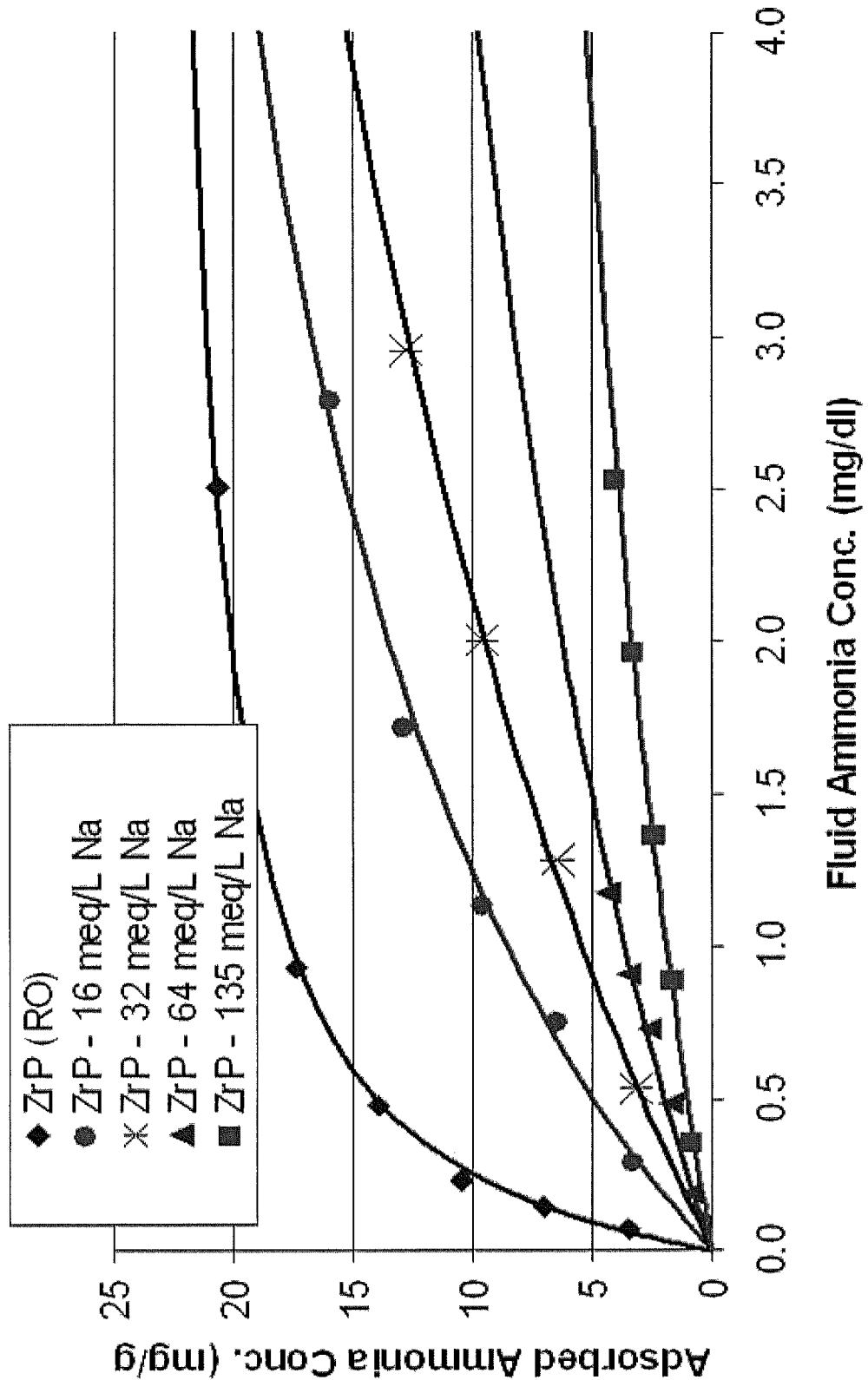
FIG. 7 is a graph of ammonia adsorbed on zirconium phosphate as a function of ammonia concentration in solutions containing 0, 16, 32, 64, or 135 mEq/L concentration of sodium.

Four beakers were labeled with sodium descriptors: "Low," "Med," "High," and "V. High." Sodium chloride was added to each beaker as follows: Low=70.4 mg; Med=134.9 mg; High=284.9 mg; V. High=571.5 mg. Then 75 g of RO water were added to each beaker and stirred to mix. Then 5 g of zirconium phosphate were added to each beaker. The first ammonia solution was prepared by mixing 0.5 mL ammonium hydroxide with 25 mL RO water (Low $NH_3$). The second ammonia solution was prepared by mixing 2 mL ammonium hydroxide with 23 mL RO water (High $NH_3$). Sequential 1 mL aliquots of Low $NH_3$ solution were added to High and V. High beakers, stirring for at least 30 minutes, and then the solution was sampled for ammonia concentration analysis prior to adding the next aliquot. Sequential 1 mL aliquots of High $NH_3$ solution were added to Low and Med beakers, stirring for at least 30 minutes, and then the solutions were sampled for ammonia concentration analysis prior to adding the next aliquot. The amount of ammonia adsorbed was determined by the difference between the amount added and the amount free in solution. FIG. 7 is a graph of ammonia adsorbed on zirconium phosphate as a function of ammonia concentration in solutions containing 0, 16, 32, 64, or 135 mEq/L concentration of sodium, showing the decrease in the ability of zirconium phosphate to adsorb ammonia with increasing sodium concentration, underscoring the importance of the cation rejecting membrane in the second cartridge.

Urea Removal with Sodium Rejecting Membrane

Figure 8:
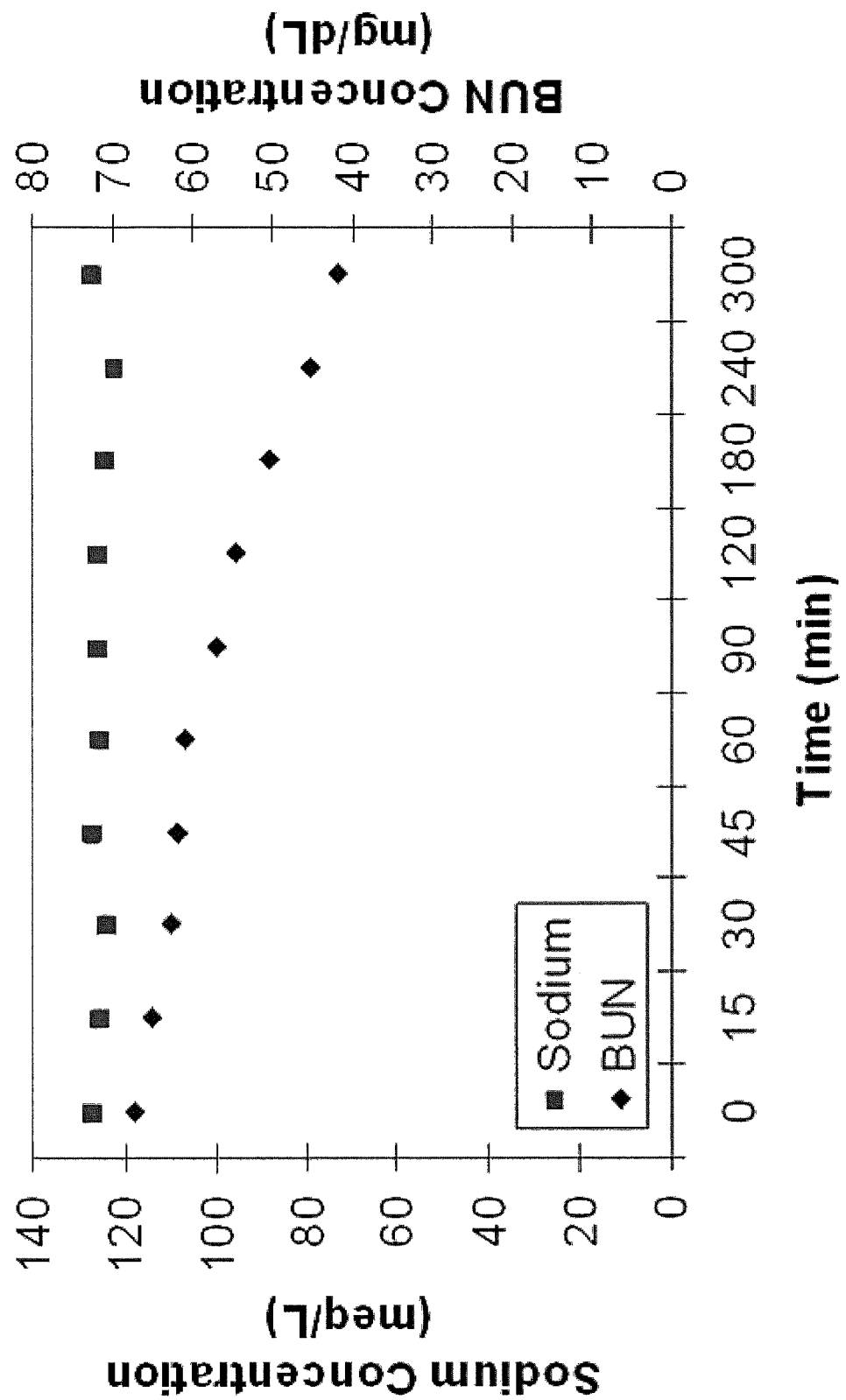
FIG. 8 is a graph of sodium and BUN concentration as a function of time in an experimental system.

The second cartridge was a dialyzer with 0.66 m² interfacial-type coated cation rejecting membrane area. A lumen (contaminated dialysate) solution was prepared containing 30.86 g sodium chloride, 1.36 g calcium chloride, 6.0 g urea, and 4 L RO water. A shell side (second cleaning) solution was prepared containing 217.42 g glucose, 2.41 g potassium chloride, and 4 L RO water. Each solution was stirred to mix and then pumped countercurrent from the beaker through the dialyzer at 100 mL/min. Samples were taken from beakers at various times for analysis using blood chemistry analyzer to measure the urea concentration, and using an ion selective electrode to measure the sodium concentration. FIG. 8 shows a graph of sodium and blood urea nitrogen (BUN) concentration as a function of time, in the dialysate, showing that urea was being removed from the dialysate over time, while sodium was retained in the dialysate by the cation rejecting hollow fibers.

Urea Breakdown with Ammonia Removal

Figure 9:
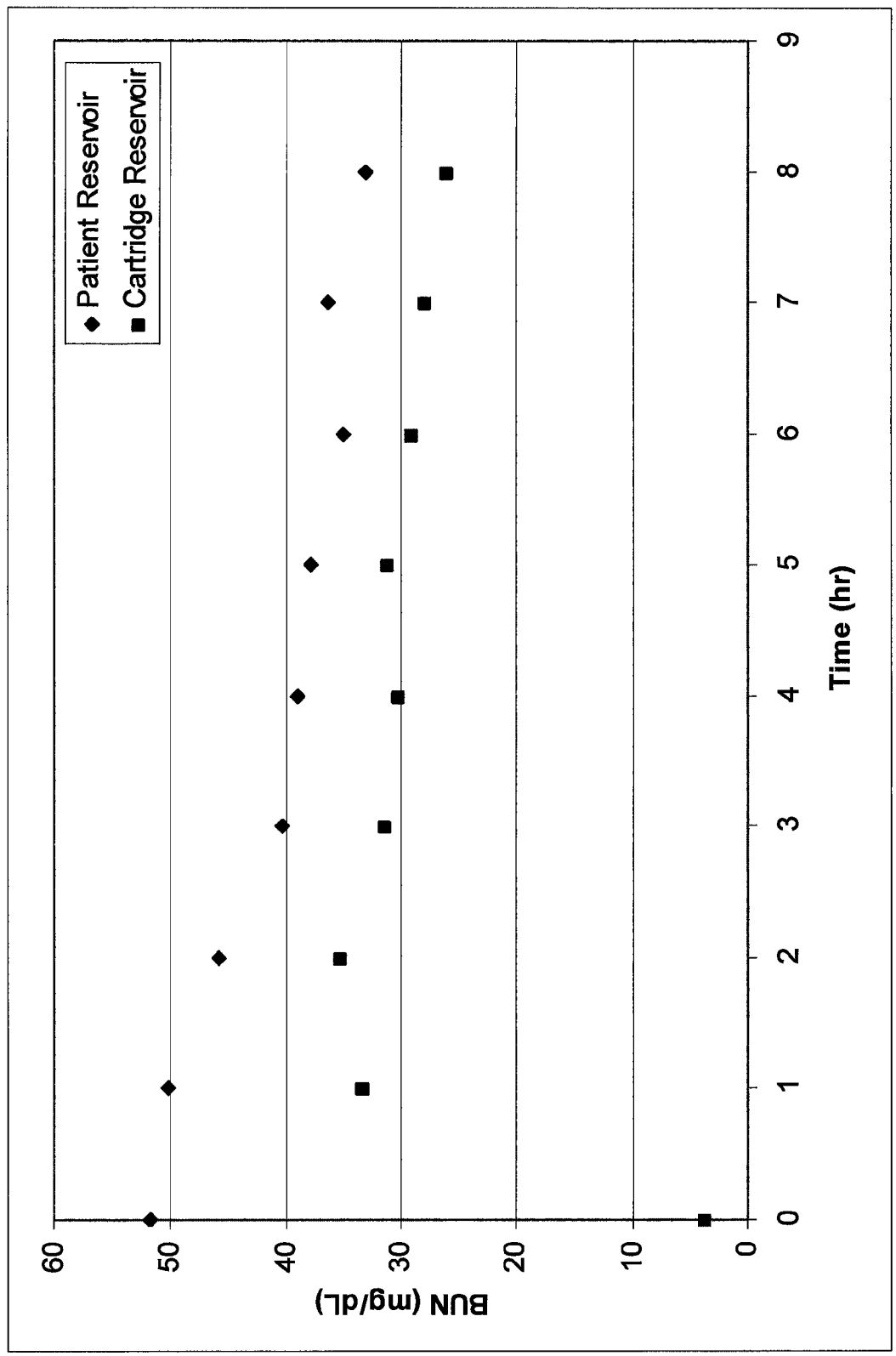
FIG. 9 is a graph of BUN concentration as a function of time in the dialysate and in the second dialysate cleaning solution in an experimental system.
Figure 10:
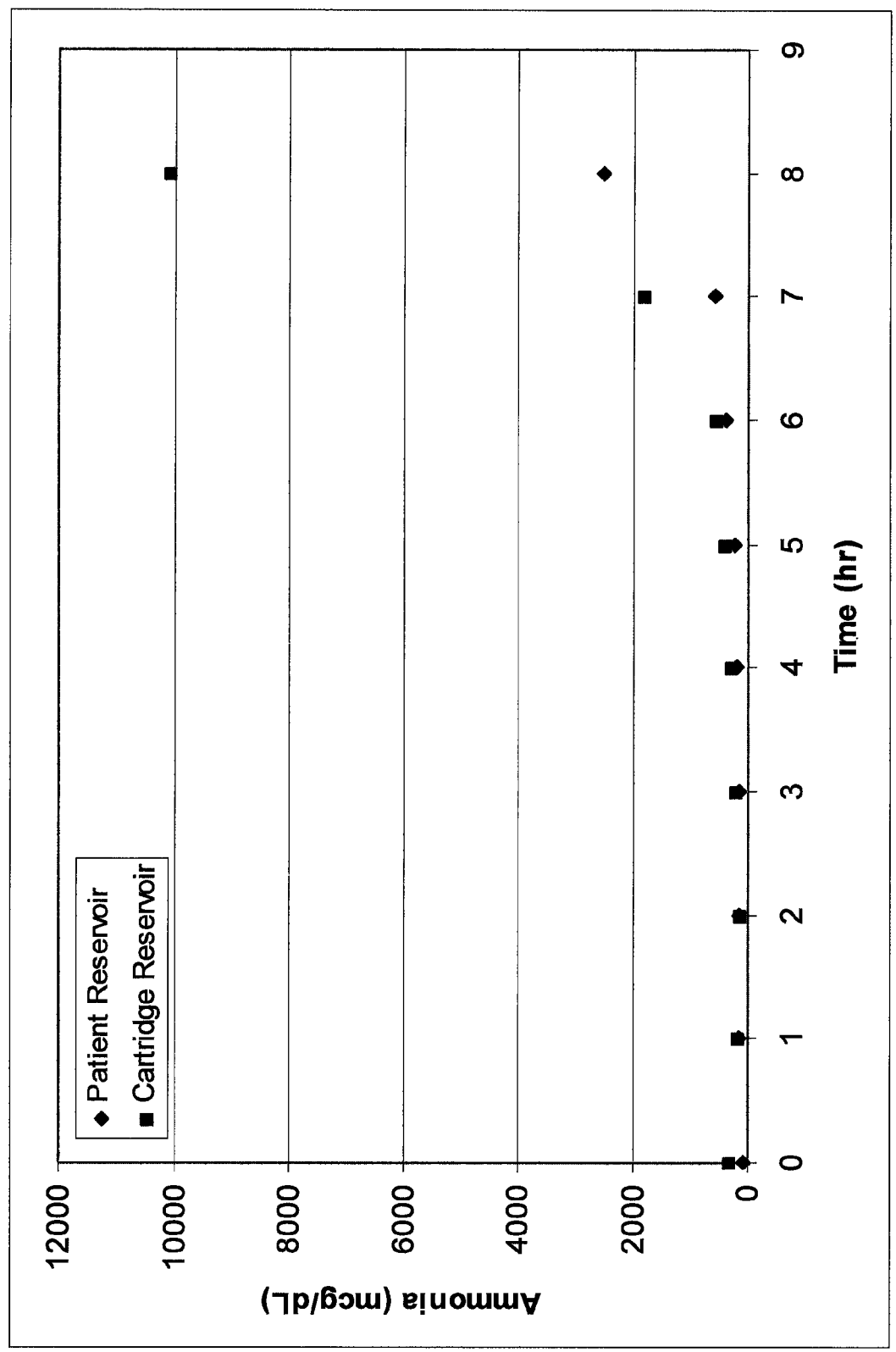
FIG. 10 is a graph of ammonia concentration as a function of time in the dialysate and in the second dialysate cleaning solution in an experimental system.

A simulated contaminated dialysate was prepared by adding 46.04 g urea to 42 L of RO water and mixing. The test cartridge contained 10.04 g of cross-linked jack bean meal and 215 g of a strong acid ion exchange material (sulfonic acid substituted polystyrene cross-linked with divinyl benzene). These two materials were in separate sequential containers, with the jack bean meal container first in the flow path followed by the ion exchange material. The cartridge reservoir contained 2 L of RO water and the dialyzer used was a Fresenius Hemoflow F40S, with a membrane area of 0.7 m². The contaminated dialysate was pumped with a peristaltic pump at a flow rate of 112 mL/min. The second cleaning solution was pumped with a gear pump at a flow rate of 214 mL/min. Both flow rates were measured via timed collection. An adjustable clamp was placed at the dialyzer lumen exit port to maintain equal hydrostatic pressure and prevent ultrafiltration. Samples were collected from each solution at various times and analyzed for urea nitrogen and ammonia concentration using an automated blood chemistry analyzer. FIG. 9 shows a graph of BUN (urea) concentration as a function of time in the dialysate (patient reservoir) and in the second dialysate cleaning solution (cartridge reservoir). FIG. 10 shows a graph of ammonia concentration as a function of time in the dialysate (patient reservoir) and in the second dialysate cleaning solution (cartridge reservoir). As shown in FIG. 9, the urea concentration in the dialysate steadily decreased over 8 hours, while the urea concentration in the second cleaning solution remained low over the 8 hours, because the urea was continually removed by the urease. As shown in FIG. 10, the ammonia concentration in both the dialysate (patient reservoir) and in the second dialysate cleaning solution (cartridge reservoir) remained low up to about 7 hours, because the strong acid ion exchange material was continually removing ammonia, and then increased as the strong acid ion exchange material became increasingly saturated.

The relevant teachings of all patents, published applications and references cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims. Specifically, while the first and second cartridges have been described as containing hollow fibers, it will be understood by those skilled in the art that other membrane configurations, such as flat sheet membranes are within the scope of the invention. In particular, the chemical and/or biological experimental data developed in in vitro or in vivo experiments (particularly in animals) or extrapolated therefrom can vary significantly from later developed values appropriate for human beings, as is known by those skilled in the art. Such later-developed values are within the routine skill of practitioners in the art using their own knowledge and the teachings set forth herein.

What is claimed is:

1. A dialysate regeneration system for removing contaminants from spent dialysate comprising:
   a) a dialysate circulation flow path including:
      i) a pump for pumping spent dialysate through the dialysate circulation flow path;
      ii) a first cartridge including semi-permeable hollow fibers for removing contaminants from the spent dialysate, and further including a first cleaning solution inlet and a first cleaning solution outlet; and
      iii) a second cartridge downstream from the first cartridge, the second cartridge including semi-permeable hollow fibers that permit transport of urea from the spent dialysate across the walls of the semi-permeable hollow fibers and are fabricated from or coated with a cation-rejecting material to retain at least calcium, magnesium, and sodium ions in the spent dialysate, and further including a second cleaning solution inlet and a second cleaning solution outlet;
   b) a first cleaning flow path including a pump for pumping a first cleaning solution from the first cartridge through a first cleaning stage and back to the first cartridge; and
   c) a second cleaning flow path downstream from the first cleaning flow path, wherein the second cleaning flow path includes a pump for pumping a second cleaning solution from the second cartridge through a second cleaning stage and back to the second cartridge.

2. The dialysate regeneration system of claim 1, wherein the first cleaning stage includes activated carbon.

3. The dialysate regeneration system of claim 2, wherein the first cleaning stage includes zirconium oxide.

4. The dialysate regeneration system of claim 3, wherein the activated carbon and zirconium oxide form a mixture.

5. The dialysate regeneration system of claim 1, wherein the first cartridge is an ultrafiltration membrane cartridge.

6. The dialysate regeneration system of claim 1, wherein the first cartridge is a microfiltration membrane cartridge.

7. The dialysate regeneration system of claim 1, wherein the second cleaning stage includes urease.

8. The dialysate regeneration system of claim 7, wherein the urease is immobilized urease.

9. The dialysate regeneration system of claim 7, wherein the second cleaning stage includes zirconium phosphate.

10. The dialysate regeneration system of claim 9, wherein the urease and zirconium phosphate are integrated into at least one cartridge.

11. The dialysate regeneration system of claim 10, wherein the second cleaning stage includes a strong acid cation exchange resin.

12. The dialysate regeneration system of claim 11, wherein the urease and strong acid cation exchange resin are integrated into at least one cartridge.

13. The dialysate regeneration system of claim 11, wherein the second cleaning stage includes an anion exchange resin.

14. The dialysate regeneration system of claim 1, wherein the first cleaning solution includes calcium, magnesium and sodium in concentrations about equal to or less than the calcium and magnesium and sodium concentrations in the spent dialysate.

15. The dialysate regeneration system of claim 1, wherein the second cleaning solution includes an osmotic agent.

16. The dialysate regeneration system of claim 15, wherein the osmotic agent includes sucrose.

17. The dialysate regeneration system of claim 1, wherein the contaminants include one or more of creatinine, β-2-microglobulin, and phosphate.

18. A dialysate regeneration system for removing contaminants from spent peritoneal dialysate comprising:
   a) a dialysate circulation flow path including:
      i) a pump for pumping spent dialysate through the dialysate circulation flow path;
      ii) a first cartridge including an ultrafiltration membrane for removing contaminants from the spent dialysate, and further including a first cleaning solution inlet and a first cleaning solution outlet; and
      iii) a second cartridge downstream from the first cartridge, the second cartridge including semi-permeable hollow fibers that permit transport of urea from the spent dialysate across the walls of the semi-permeable hollow fibers and are fabricated from or coated with a cation-rejecting material to retain at least calcium, magnesium, and sodium ions in the spent dialysate, and further including a second cleaning solution inlet and a second cleaning solution outlet;
   b) a first cleaning flow path including a pump for pumping first cleaning solution from the first cartridge through a first cleaning stage, the first cleaning stage including a mixture of activated carbon and zirconium oxide, and back to the first cartridge; and
   c) a second cleaning flow path downstream from the first cleaning flow path, wherein the second cleaning flow path includes a pump for pumping second cleaning solution from the second cartridge through a second cleaning stage, the second cleaning stage including immobilized urease and zirconium phosphate, and back to the second cartridge.

19. A peritoneal dialysis and dialysate regeneration system comprising:
   a) a dialysate circulation flow path including:
      i) a first cartridge including semi-permeable hollow fibers for removing contaminants from spent dialysate, and further including a first cleaning solution outlet and a first cleaning solution inlet;
      ii) a second cartridge downstream from the first cartridge, the second cartridge including semi-permeable hollow fibers that permit transport of urea from the spent dialysate across the walls of the semi-permeable hollow fibers and are fabricated from or coated with a cation-rejecting material to retain at least calcium, magnesium, and sodium ions in the spent dialysate, and further including a second cleaning solution inlet and a second cleaning solution outlet; and
      iii) a peritoneal dialysis cycler configured to transfer a predetermined quantity of dialysate into a peritoneal cavity of a patient, direct spent dialysate from the peritoneal cavity of the patient into the first cartridge and the second cartridge, and introduce regenerated dialysate into the peritoneal cavity of the patient;
   b) a first cleaning flow path including a pump for pumping first cleaning solution from the first cartridge through a first cleaning stage and back to the first cartridge; and
   c) a second cleaning flow path downstream from the first cleaning flow path, wherein the second cleaning flow path includes a pump for pumping second cleaning solution from the second cartridge through a second cleaning stage and back to the second cartridge.

20. A peritoneal dialysis system for treating a patient and removing contaminants from spent dialysate comprising:
   a) a dialysate circulation flow path including:
      i) a patient dialysate outlet from a peritoneal cavity of the patient;
      ii) a pump for pumping spent dialysate from the patient dialysate outlet through the dialysate circulation flow path;
      iii) a first cartridge including semi-permeable hollow fibers for removing contaminants from the spent dialysate, and further including a first cleaning solution inlet and a first cleaning solution outlet;
      iv) a second cartridge downstream from the first cartridge, the second cartridge including semi-permeable hollow fibers that permit transport of urea from the spent dialysate across the walls of the semi-permeable hollow fibers and are fabricated from or coated with a cation-rejecting material to retain at least calcium, magnesium, and sodium ions in the spent dialysate, and further including a second cleaning solution inlet and a second cleaning solution outlet; and
      v) a patient dialysate inlet back to the peritoneal cavity of the patient;
   b) a first cleaning flow path including a pump for pumping first cleaning solution from the first cartridge through a first cleaning stage and back to the first cartridge; and
   c) a second cleaning flow path downstream from the first cleaning flow path, wherein the second cleaning flow path includes a pump for pumping second cleaning solution from the second cartridge through a second cleaning stage and back to the second cartridge.

21. A method of removing contaminants from spent dialysate comprising:
   a) flowing dialysate through a dialysate circulation flow path including:
      i) a pump for pumping spent dialysate through the dialysate circulation flow path;
      ii) a first cartridge including semi-permeable hollow fibers for removing contaminants from the spent dialysate, and further including a first cleaning solution inlet and a first cleaning solution outlet; and iii) a second cartridge downstream from the first cartridge, the second cartridge including semi-permeable hollow fibers that permit transport of urea from the spent dialysate across the walls of the semi-permeable hollow fibers and are fabricated from or coated with a cation-rejecting material to retain at least calcium, magnesium, and sodium ions in the spent dialysate, and further including a second cleaning solution inlet and a second cleaning solution outlet;

b) flowing first cleaning solution through a first cleaning flow path including a pump for pumping first cleaning solution from the first cartridge through a first cleaning stage and back to the first cartridge; and c) flowing second cleaning solution through a second cleaning flow path that is downstream from the first cleaning flow path, wherein the second cleaning flow path includes a pump for pumping second cleaning solution from the second cartridge through a second cleaning stage and back to the second cartridge.

22. The method of claim 21, wherein the first cartridge includes an ultrafiltration membrane, the first cleaning stage includes a mixture of activated carbon and zirconium oxide, and the second cleaning stage includes immobilized urease and zirconium phosphate.

23. A method of peritoneal dialysis and regenerating spent dialysate comprising:
a) flowing dialysate through a dialysate circulation flow path including:
   i) a first cartridge including semi-permeable hollow fibers for removing contaminants from the spent dialysate, and further including a first cleaning solution outlet and a first cleaning solution inlet;
   ii) a second cartridge downstream from the first cartridge, the second cartridge including semi-permeable hollow fibers that permit transport of urea from the spent dialysate across the walls of the semi-permeable hollow fibers and are fabricated from or coated with a cation-rejecting material to retain at least calcium, magnesium, and sodium ions in the spent dialysate, and further including a second cleaning solution inlet and a second cleaning solution outlet; and
   iii) a peritoneal dialysis cycler configured to transfer a predetermined quantity of dialysate into a peritoneal cavity of a patient, direct spent dialysate from the peritoneal cavity of the patient into the first cartridge and the second cartridge, and introduce regenerated dialysate into the peritoneal cavity of the patient;
b) flowing first cleaning solution through a first cleaning flow path including a pump for pumping first cleaning solution from the first cartridge through a first cleaning stage and back to the first cartridge; and
c) flowing second cleaning solution through a second cleaning flow path that is downstream from the first cleaning flow path, wherein the second cleaning flow path includes a pump for pumping second cleaning solution from the second cartridge through a second cleaning stage and back to the second cartridge.

24. A method of treating a patient and removing contaminants from spent dialysate comprising:
a) flowing dialysate through a dialysate circulation flow path including:
   i) a patient dialysate outlet from a peritoneal cavity of the patient;
   ii) a pump for pumping spent dialysate from the patient dialysate outlet through the dialysate circulation flow path;
   iii) a first cartridge including semi-permeable hollow fibers for removing contaminants from the spent dialysate, and further including a first cleaning solution inlet and a first cleaning solution outlet;
   iv) a second cartridge downstream from the first cartridge, the second cartridge including semi-permeable hollow fibers that permit transport of urea from the spent dialysate across the walls of the semi-permeable hollow fibers and are fabricated from or coated with a cation-rejecting material to retain at least calcium, magnesium, and sodium ions in the spent dialysate, and further including a second cleaning solution inlet and a second cleaning solution outlet; and
   v) a patient dialysate inlet back to the peritoneal cavity of the patient;
b) flowing first cleaning solution through a first cleaning flow path including a pump for pumping first cleaning solution from the first cartridge through a first cleaning stage and back to the first cartridge; and
c) flowing second cleaning solution through a second cleaning flow path that is downstream from the first cleaning flow path, wherein the second cleaning flow path includes a pump for pumping second cleaning solution from the second cartridge through a second cleaning stage and back to the second cartridge.

* * * * *